(12) United States Patent
Astrom et al.

(10) Patent No.: US 10,300,285 B2
(45) Date of Patent: May 28, 2019

(54) IMPEDANCE-BASED ALLOCATION OF ELECTRICAL STIMULATION TO ELECTRODE CLUSTERS

(71) Applicant: Medtronic Bakken Research Center B.V., Maastricht (NL)

(72) Inventors: Mattias Bengt Johan Astrom, Vasteras (SE); Mark Hage, Eindhoven (NL); Hubert Cecile François Martens, Eindhoven (NL); Kambiz Nanbakhsh, Eindhoven (NL); Erik van Veenendaal, Nuenen (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 108 days.

(21) Appl. No.: 15/399,089

(22) Filed: Jan. 5, 2017

(65) Prior Publication Data

US 2018/0185651 A1   Jul. 5, 2018

(51) Int. Cl.
  A61N 1/00    (2006.01)
  A61N 1/36    (2006.01)
  A61N 1/372   (2006.01)
  A61N 1/05    (2006.01)
(52) U.S. Cl.
  CPC ....... *A61N 1/36185* (2013.01); *A61N 1/3614* (2017.08); *A61N 1/37247* (2013.01); *A61N 1/0534* (2013.01); *A61N 1/36064* (2013.01); *A61N 1/36067* (2013.01); *A61N 1/36082* (2013.01)
(58) Field of Classification Search
  None
  See application file for complete search history.

(56) References Cited

U.S. PATENT DOCUMENTS

| 6,978,171 B2 | 12/2005 | Goetz et al. |
| 7,317,948 B1 | 1/2008 | King et al. |
| 7,742,823 B2 | 6/2010 | King et al. |
| 8,108,049 B2 | 1/2012 | King |
| 8,229,151 B2 | 7/2012 | Saltykov et al. |
| 8,265,766 B1 | 9/2012 | Kulkarni et al. |
| 8,527,058 B2 | 9/2013 | Kulkarni et al. |
| 8,583,253 B1 | 11/2013 | Shi et al. |
| 8,751,006 B2 | 6/2014 | Saoji et al. |
| 8,788,056 B2 | 7/2014 | King et al. |

(Continued)

*Primary Examiner* — Christopher Koharski
*Assistant Examiner* — Elizabeth K So
(74) *Attorney, Agent, or Firm* — Shumaker & Sieffert, P.A.

(57) ABSTRACT

Electrical stimulation sources and amplitudes are allocated to implantable electrodes based on impedance values for controlled delivery of electrical stimulation therapy to a patient. Allocation may include assigning implantable electrodes, in a group of active electrodes, to clusters based on impedance values of the electrodes, coupling the electrode clusters to respective stimulation sources, and defining respective stimulation amplitudes delivered by the stimulation sources to the electrode clusters. Each cluster may include electrodes having relatively similar impedance values, such that electrodes in each cluster present less variation in impedance relative to impedance variation across the group of electrodes. With reduced variation in impedance, in some examples, variation in current outflow through electrodes in each cluster may be reduced, promoting more uniform distribution of stimulation current across the group of active electrodes and a more uniform stimulation field.

41 Claims, 11 Drawing Sheets

(56) References Cited

U.S. PATENT DOCUMENTS

| | | |
|---|---|---|
| 8,825,175 B2 | 9/2014 | King |
| 9,089,704 B2 | 7/2015 | Kelly |
| 9,089,706 B2 | 7/2015 | King et al. |
| 9,205,263 B2 | 12/2015 | King et al. |
| 9,238,135 B2 | 1/2016 | Goetz et al. |
| 9,403,015 B2 | 8/2016 | Hershey |
| 9,572,987 B2 | 2/2017 | Martens |
| 2003/0176807 A1 | 9/2003 | Goetz et al. |
| 2009/0276010 A1 | 11/2009 | Goetz et al. |
| 2010/0262209 A1 | 10/2010 | King et al. |
| 2011/0060387 A1 | 3/2011 | King et al. |
| 2012/0109254 A1 | 5/2012 | King |
| 2013/0006324 A1 | 1/2013 | Bradley |
| 2013/0211478 A1 | 8/2013 | Kelly |
| 2013/0282077 A1 | 10/2013 | Saoji et al. |
| 2014/0296941 A1 | 10/2014 | King et al. |
| 2015/0112321 A1 | 4/2015 | Cadouri |
| 2015/0224316 A1 | 8/2015 | Martens |
| 2015/0265838 A1 | 9/2015 | Kals et al. |
| 2016/0144189 A1 | 5/2016 | Bakker et al. |
| 2016/0303380 A1 | 10/2016 | Hershey |

| RING | MEDIAL | POSTERIOR | LATERAL | ANTERIOR |
|---|---|---|---|---|
| 1 | 5068 | 5406 | 5744 | 6081 |
| 2 | 6314 | 6647 | 6979 | 7312 |
| 3 | 7634 | 7966 | 8298 | 8630 |
| 4 | 8957 | 9289 | 9621 | 9953 |

IMPEDANCE (OHMS) BETWEEN EACH ELECTRODE AND IPG

| | ONE SOURCE | | | |
|---|---|---|---|---|
| RING | MEDIAL | POSTERIOR | LATERAL | ANTERIOR |
| 1 | 0.24 | 0.22 | 0.20 | 0.18 |
| 2 | 0.13 | 0.11 | 0.10 | 0.09 |
| 3 | 0.09 | 0.09 | 0.08 | 0.07 |
| 4 | 0.11 | 0.10 | 0.09 | 0.09 |

CURRENT DISTRIBUTION WITHOUT IMPEDANCE-BASED ALLOCATION OF STIMULATION SOURCES

FIG. 7

| | IMPEDANCE-BASED ALLOCATION OF SOURCES | | | |
|---|---|---|---|---|
| RING | MEDIAL | POSTERIOR | LATERAL | ANTERIOR |
| 1 | 0.15 | 0.13 | 0.12 | 0.10 |
| 2 | 0.18 | 0.16 | 0.15 | 0.14 |
| 3 | 0.12 | 0.11 | 0.10 | 0.09 |
| 4 | 0.13 | 0.11 | 0.11 | 0.10 |

CURRENT DISTRIBUTION WITH IMPEDANCE-BASED ALLOCATION OF STIMULATION SOURCES

FIG. 8

IMPEDANCE-BASED ALLOCATION OF ELECTRICAL STIMULATION TO ELECTRODE CLUSTERS

TECHNICAL FIELD

This disclosure relates to implantable medical devices and, more particularly, delivery of electrical stimulation therapy via implantable medical devices.

BACKGROUND

Medical devices may be external or implantable, and may be used to deliver electrical stimulation therapy to various tissue sites of a patient to treat a variety of symptoms or conditions. A medical device may deliver electrical stimulation therapy via one or more implantable leads that place electrodes proximate to target locations in a patient. Examples of target locations include anatomical structures in the brain for deep brain stimulation (DBS), the spinal cord for spinal cord stimulation (SCS), pelvic nerves for pelvic stimulation, nerves in the gastrointestinal tract for gastric stimulation, and various peripheral nerves for peripheral nerve field stimulation (PNFS).

A clinician may select values for a number of programmable parameters in order to define the electrical stimulation therapy to be delivered to a patient. For example, the clinician may select two or more active electrodes for delivery of the stimulation, polarities of the electrodes, voltage or current pulse amplitude, stimulation pulse width, and stimulation pulse frequency as stimulation parameters. The clinician may select these parameters to locate, direct and shape stimulation fields, e.g., to provide stimulation that promotes therapeutic efficacy while avoiding or suppressing undesirable side effects.

SUMMARY

In general, the disclosure describes example techniques, devices and systems for impedance-based allocation of electrical stimulation sources and amplitudes to implantable electrodes for delivery of electrical stimulation therapy to a patient. The techniques may include assigning implantable electrodes, in a group of active electrodes, to electrode clusters based on impedance values of the electrodes, coupling the electrode clusters to respective stimulation sources, and defining respective stimulation amplitudes delivered by the stimulation sources to the electrode clusters. Each electrode cluster may include electrodes having relatively similar impedance values, such that electrodes in each cluster present less variation in impedance relative to impedance variation between electrodes of the group of electrodes. With reduced variation in impedance between the electrodes of a cluster, in some examples, variation in current outflow through electrodes in each cluster may be reduced, promoting more uniform distribution of stimulation current across the group of active electrodes and a more uniform stimulation field.

In one example, the disclosure describes a method for delivering electrical stimulation to a patient via a plurality of implantable electrodes of an implantable medical device (IMD), the method comprising delivering a first portion of the electrical stimulation from a first electrical stimulation source of the IMD via a first cluster of one or more electrodes selected based on impedance values of the one or more electrodes in the first cluster, the first cluster of one or more electrodes being in a group of the plurality of implantable electrodes selected for delivery of the electrical stimulation and comprising less than all of the electrodes in the group, and delivering a second portion of the electrical stimulation from a second electrical stimulation source of the IMD via a second cluster of one or more electrodes selected based on impedance values of the one or more electrodes in the second cluster, the second cluster of one or more electrodes being in the group of the plurality of implantable electrodes, being different than the first cluster of one or more electrodes and comprising less than all of the electrodes in the group.

In another example, the disclosure describes an implantable medical device (IMD) for delivering electrical stimulation to a patient, the IMD comprising a plurality of implantable electrodes, a first electrical stimulation source, a second electrical stimulation source, and one or more processors configured to control the first electrical stimulation source to deliver a first portion of the electrical stimulation via a first cluster of one or more electrodes selected based on impedance values of the one or more electrodes in the first cluster, the first cluster of one or more electrodes being in a group of the plurality of implantable electrodes selected for delivery of the electrical stimulation and comprising less than all of the electrodes in the group, and control the second electrical stimulation source to deliver a second portion of the electrical stimulation via a second cluster of one or more electrodes selected based on impedance values of the one or more electrodes in the second cluster, the second cluster of one or more electrodes being in the group of the plurality of implantable electrodes, being different than the first cluster of one or more electrodes and comprising less than all of the electrodes in the group.

In another example, the disclosure describes a system for delivering electrical stimulation to a patient, the system comprising an implantable medical device (IMD) comprising a plurality of implantable electrodes, a first electrical stimulation source, a second electrical stimulation source, and one or more processors configured to control the first electrical stimulation source to deliver a first portion of the electrical stimulation via a first cluster of one or more electrodes selected based on impedance values of the one or more electrodes in the first cluster, the first cluster of one or more electrodes being in a group of the plurality of implantable electrodes selected for delivery of the electrical stimulation and comprising less than all of the electrodes in the group, and control the second electrical stimulation source to deliver a second portion of the electrical stimulation via a second cluster of one or more electrodes selected based on impedance values of the one or more electrodes in the second cluster, the second cluster of one or more electrodes being in the group of the plurality of implantable electrodes, being different than the first cluster of one or more electrodes and comprising less than all of the electrodes in the group, and an external programmer comprising one or more processors configured to program one or more parameters of the electrical stimulation delivered by the IMD, wherein one or more processors of at least one of the IMD or the external programmer are configured to select the group of the plurality of implantable electrodes of the IMD for delivery of the electrical stimulation to the patient, select the first cluster of one or more of the electrodes in the group of the plurality of implantable electrodes based on the impedance values of the one or more electrodes in the first cluster, and select the second cluster of one or more of the electrodes in the group of the plurality of implantable electrodes based on the impedance values of the one or more electrodes in the second cluster.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIG. 7 is a table illustrating an example of current distribution values for the group of active electrodes shown in FIG. 6A when impedance-based allocation of stimulation sources is not used and the electrodes are driven by one stimulation source.

FIG. 8 is a table illustrating an example of current distribution values for the group of active electrodes shown in FIG. 6A when impedance-based allocation of stimulation sources is used and clusters of the electrodes are driven with different stimulation sources.

DETAILED DESCRIPTION

Figure 1:
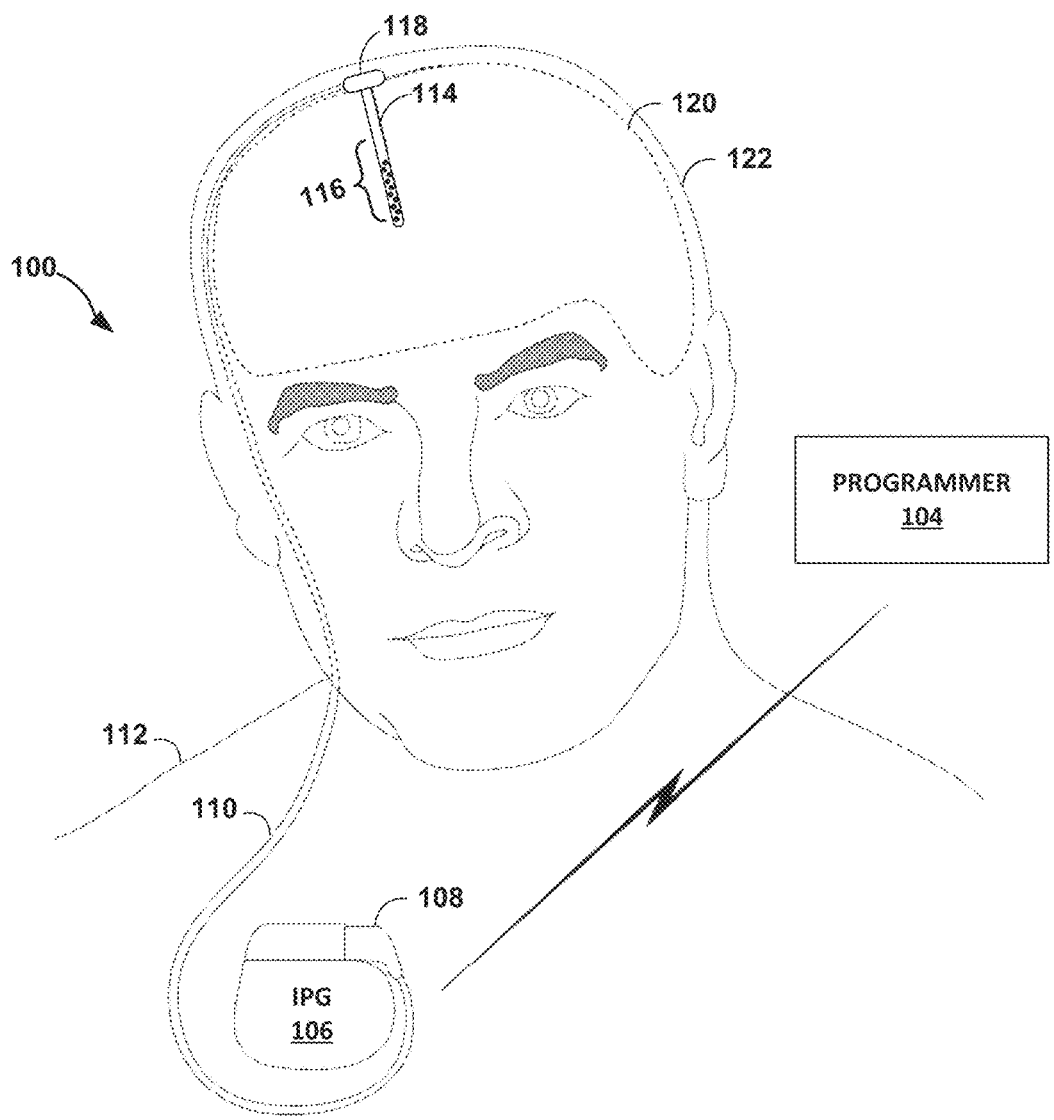
FIG. 1 is a conceptual diagram illustrating a system including an implantable medical device (IMD) configured to deliver electrical deep brain stimulation (DBS) therapy to a patient in accordance with an example of the disclosure.

Electrical stimulation can be an effective therapy for a variety of diseases or disorders such as Parkinson's disease, epilepsy, chronic pain, gastroparesis, incontinence, sexual dysfunction, and migraine headaches. An IMD may be configured to deliver electrical stimulation therapy via implantable electrodes to a variety of target locations. Some electrical stimulation devices, also referred to as neurostimulation or neuromodulation devices, may have a relatively large number of electrodes that permit precise control of delivery of electrical stimulation to target locations.

Deep brain stimulation (DBS) will be described for purposes of example, although the techniques, devices and systems described in this disclosure may be more generally applicable to a variety of stimulation therapies, such as spinal cord stimulation (SCS) (including dorsal column stimulation), pelvic stimulation, gastric stimulation or peripheral nerve field stimulation (PNFS). The techniques described in this disclosure also may be applicable to other types of electrical stimulation, such as cardiac stimulation, cochlear stimulation, or functional electrical stimulation (FES). Accordingly, the techniques, devices and systems described in this disclosure should not be considered limited to DBS.

To reduce the variability of current outflow on individual electrodes within a group of electrodes, this disclosure describes, in various examples, techniques for using information from impedance measurements during allocation of stimulation amplitude sources to active electrodes. In some examples, the influence of patient-specific tissue properties on current distribution may be reduced, resulting in a more uniform stimulation field delivered to the tissue, and more precise control over the stimulation field.

DBS may be an effective neurosurgical therapy for Parkinson's disease, other movement disorders, and other brain disorders such as epilepsy. One or more DBS leads may be implanted with stereotactic techniques in deep regions of the brain of a patient. Chronic electrical stimulation may be delivered via selected electrodes among an array of electrodes carried by the lead or leads. The electrical stimulation may be delivered to the electrodes from one or more battery-powered stimulation sources, which may be housed in an implantable pulse generator (IPG) that is implantable in the patient, e.g., at a subcutaneous or submuscular location inferior from the clavicle. A lead extension, which may extend from the IPG to a lead coupling device mountable in a burr hole in the cranium of the patient, may connect a distal, implantable lead (which may also be referred to as an implantable probe) to the stimulation sources in the IPG. The IPG, lead extension, lead and electrodes together form an example of an IMD.

The clinical benefit of DBS, and some other electrical stimulation therapies, may be dependent on the spatial distribution of an electric field, generated by the stimulation delivered by the selected electrodes, in relation to brain anatomy. Precise control over the stimulation field can help to promote therapeutic benefits while avoiding unwanted side-effects. In some examples, precise control of the stimulation field may involve the use of higher resolution electrode arrays, such as arrays of so-called segmented electrodes that may provide a relatively high number of individual electrodes, not only at various axial positions along a lead, but also at various circumferential positions around the lead. Selection of electrodes at a wider variety of spatial locations may permit precise location, sizing and shaping of the stimulation field relative to anatomical targets, such as particular brain structures.

Some high resolution electrical stimulation devices may have a large number (e.g., 40 or more) of electrodes at which stimulation current can be delivered. Battery-operated pulse generators that deliver stimulation current to the electrodes may have a finite number of stimulation amplitude sources. In particular, some stimulation devices may not provide a one-to-one mapping between stimulation source and electrode, where each electrode has its own stimulation source. During stimulation therapy with high resolution DBS leads, a multitude of electrodes may be active during stimulation, which is different than some stimulation therapies with leads where one electrode may be used to deliver stimulation. In the case where the number of active electrodes is larger than the number of available stimulation sources, more than one electrode will be connected to the same stimulation amplitude source. In particular, a group of multiple electrodes may be connected to a single stimulation amplitude source, e.g., such that the output of the single stimulation source is delivered to the electrodes in the group in parallel.

Due to tissue heterogeneity and anisotropy, the spreading resistance (as well as electronic resistances for each electrode) may be different for different electrodes within a group of electrodes coupled to a stimulation source. With a current-controlled stimulation system, where the total current output of each stimulation source is regulated, the current outflow may be different for different electrodes coupled to the stimulation source. In particular, when a stimulation source delivers stimulation current with a regulated current amplitude in parallel across multiple electrodes in the cluster, the amount of current delivered by each electrode may vary due to impedance differences among the electrodes.

Variation in impedance among the electrodes in a group of electrodes coupled to the same stimulation source may result in excessive delivery of stimulation current to certain electrodes (i.e., electrodes with lower impedance) and insufficient delivery of stimulation current to other electrodes (i.e., electrodes with higher impedance) within that group. Consequently, there may be significant variation in the levels of stimulation current outflow from individual electrodes in the group, which in turn may cause uneven distribution of the stimulation field. Uneven distribution of the stimulation field may impact the ability to precisely control the location, shape and size of the stimulation field. In addition, in some cases, this variation could impact charge density safety limits, where the amount of current delivered via a particular electrode with lower impedance could be undesirably high.

To reduce variability of current outflow on individual electrodes within a cluster, this disclosure describes, in various examples, techniques for allocating electrical stimulation sources and amplitudes to implantable electrodes based on impedance values associated with the respective electrodes, which may allow an electrical stimulation system to provide more controlled delivery of electrical stimulation therapy to a patient. The techniques may include assigning implantable electrodes, in a group of active electrodes, to two or more respective electrode clusters based on impedance values of the electrodes, coupling the electrode clusters to respective stimulation sources, and defining respective stimulation amplitudes delivered by the stimulation sources to the electrode clusters. In general, an active electrode may be an electrode that is selected for delivery of electrical stimulation, whereas an inactive electrode is not selected for delivery of electrical stimulation. Hence, an active electrode may be considered to be "on" and coupled to an active stimulation source that generates electrical stimulation current, whereas an inactive electrode may be considered to be "off" and not coupled to an active stimulation source that generates electrical stimulation current.

Each electrode cluster may include electrodes having relatively similar impedance values, such that electrodes in each cluster present less variation in impedance relative to impedance variation across electrodes of the group of electrodes. In some examples, a clustering algorithm, such as a k-means clustering algorithm, may be used to assign the electrodes to clusters based on impedance values measured for the electrodes. With reduced variation in impedance, in some examples, variation in current outflow through electrodes in each cluster may be reduced, which may promote more uniform distribution of stimulation current across the group of active electrodes and a more uniform stimulation field.

An IMD may be configured to use information from impedance measurements during allocation of stimulation sources and stimulation amplitudes to active electrodes. In some examples, the IMD may measure impedance prior to commencing delivery of stimulation with an electrical stimulation device. Impedance also may be measured or re-measured at various times to account for changes in impedance, permitting re-clustering (i.e., modified clustering) of electrodes, re-allocation of stimulation sources to electrode clusters, and/or re-definition of stimulation amplitudes for electrode clusters based on electrode impedance changes. For example, measurement, clustering and allocation may be performed by an IMD during clinic visits to a clinician by a patient, upon remote interrogation and programming by a clinician, at regular or scheduled intervals, and/or in response to sensed events or conditions.

By clustering electrodes based on the measured impedance values of the individual electrodes, the variability of current outflow on individual electrodes within a cluster can be reduced. Impedance-based allocation of stimulation sources to clusters may then be applied in such a way that electrodes with similar impedances are clustered together and coupled to the same stimulation source. For example, a first cluster of electrodes (forming part of a group of active electrodes) may be coupled to a first stimulation source, while a second cluster of electrodes (forming another part of the group of active electrodes) may be coupled to a second stimulation source. A cluster of the electrodes may include a plurality of, i.e., two or more, electrodes assigned to a cluster based on impedance values of the electrodes. In some examples, a cluster of the electrodes may have a single electrode assigned to the cluster based on an impedance value of the electrode. Accordingly, although clusters of electrodes may include clusters of two or more electrodes, in some examples, one or more of the clusters may each include a single electrode, depending upon the result of impedance-based allocation of electrodes to the clusters.

The first electrode cluster may include different electrodes than the electrodes in the second electrode cluster. For example, the electrode or electrodes in the first cluster and the electrode or electrodes in the second cluster may be mutually exclusive, e.g., such that no electrode in the first cluster resides in the second cluster and no electrode in the second cluster resides in the first cluster. The number of electrodes in each of the first and second clusters may be the same or different, and may be less than the number of electrodes in the group of active electrodes. Each of the two or more clusters formed by the impedance-based allocation technique may have a plurality of electrodes of the group of electrodes. For example, a first cluster may comprise a first plurality of the electrodes in the group of the electrodes and a second cluster may comprise a second plurality of the electrodes in the group of electrodes. In other examples, clustering could produce at least one cluster comprising a single electrode of the group of the electrodes, and one or more other clusters may have a plurality of electrodes of the group of the electrodes. In further examples, generation of clusters with single electrodes could be excluded from the impedance-based allocation process, such that all clusters resulting from the impedance-based allocation process have multiple electrodes and no clusters have only a single electrode. For example, generation of clusters with single electrodes could be excluded for larger sets of electrodes, but permitted for smaller sets of electrodes.

The sum of the number of electrodes in the first cluster and the number of electrodes in the second cluster may be equal to the number of electrodes in the group of active electrodes. In some examples, electrodes in the group of active electrodes may be assigned to more than two clusters, such as three clusters, four clusters, or more. The electrodes in each of the two or more clusters may be different from one another and form part of the group of active electrodes. Hence, in cases of three, four or more clusters, as in the case of two clusters, the electrodes in the clusters may be mutually exclusive, each cluster may include less than all of the group of active electrodes, the clusters may have a same or different number of electrodes, and a sum of the numbers of electrodes in the clusters may be equal to a number of electrodes in the group of active electrodes.

The first and second stimulation sources may include electrical circuitry for generating electrical stimulation pulse waveforms with pulses having regulated voltage amplitudes or regulated current amplitudes. The first and second stimulation sources may be independent stimulation sources that are capable of delivering pulses with different stimulation amplitudes, e.g., different regulated voltage amplitudes or different regulated current amplitudes, to the first and second electrode clusters at the same time or substantially the same time. The amplitudes delivered by the stimulation sources to the electrode clusters (e.g., two or more clusters) may sum to a total desired amplitude to be delivered via the group of active electrodes.

The stimulation amplitudes delivered by the stimulation sources may be different or the same. If there are different numbers of electrodes in the first and second clusters, the stimulation amplitudes delivered by the respective stimulation sources to the clusters will ordinarily be different. If the clusters have the same number of electrodes, the stimulation amplitudes delivered by the respective stimulation sources to the clusters will ordinarily be the same or substantially the same.

If there are more than two clusters, then more than two stimulation sources may be coupled, respectively, to the electrode clusters (e.g., one source to each cluster), commensurate with the number of clusters. The stimulation amplitudes delivered by more than two stimulation sources may be the same or substantially the same when the number of electrodes in each cluster is the same, or different when the number of electrodes in each of the clusters is different.

Clustering electrodes with respect to stimulation sources and stimulation amplitudes based on impedance may promote a more uniform current distribution across the larger group of active electrodes. For example, the influence of patient-specific tissue properties on the current distribution may be reduced, a more uniform stimulation field may be delivered to the tissue, and control over the stimulation field may be more precise.

Techniques for impedance-based clustering of electrodes, in accordance with examples of this disclosure, may comprise clustering of electrodes, allocation of stimulation sources to the clusters, and definition of stimulation amplitudes to be delivered from the stimulation sources to the electrodes in each cluster. Electrodes may be clustered based on impedance measurements carried out between each electrode and a reference electrode, which also may be referred to as a return electrode or a ground electrode. The reference electrode may be on an IMD case, e.g., of an IPG, on a lead carrying one or more of the active electrodes (e.g., as a dedicated reference electrode or as any of the other electrodes carried by the lead, which may be selectively coupled to a reference node of the stimulation sources in the IPG), or on another component coupled between the IPG and the lead.

Hence, each of the impedance values of the electrodes on the lead may be an impedance value measured between the respective electrode on the lead and a reference electrode disposed on a case of the IPG, between the respective electrode on the lead and a reference electrode on the lead, or between the respective electrode on the lead and a reference electrode positioned between the IPG and the lead, e.g., on a lead coupler that couples a proximal end of the lead to a distal end of a lead extension. For an example in which the reference electrode is formed on the lead with the electrodes for which impedance is to be measured, the reference electrode may be a dedicated reference electrode, such as a contact, ring or coil formed on the lead, or the reference electrode may be formed by one or more of the electrodes carried by the lead to deliver stimulation, in which case a switch device may selectively couple the electrode or electrodes to a reference node of the stimulation source circuitry to form one or more reference electrodes.

In some examples, impedance may be measured between electrodes on the lead, e.g., providing inter-electrode impedance values between all or some of the active electrodes. For example, inter-electrode impedance values measured between each active electrode and other electrodes on a lead (or current distribution values determined based on a desired stimulation amplitude and the impedance values) may be used to cluster the electrodes, allocate stimulation sources to the clusters, and define stimulation amplitudes to be delivered from the stimulation sources to the electrodes in each cluster.

In one example, clustering of electrodes may be carried out by first simulating the distribution of electrical currents from one stimulation source connected to all the active electrodes in the group of active electrodes, given the measured impedance values of the active electrodes. The resulting per-electrode current distributions may then be partitioned using an algorithm, such as a k-means clustering algorithm, where each of the electrodes is binned into one of two or more clusters having a mean current distribution value that is nearest to the current distribution value of the respective electrode. As the current distribution value of an electrode is based on the impedance value of the electrode, in this example, the clustering of the electrode based on the current distribution value is based on the impedance value of the electrode.

The simulated current distribution for an electrode may be determined, for example, based on the overall current to be delivered in parallel to the electrodes in the group of active electrodes and the impedance value of the electrode relative to the impedance values of the other electrodes in the group of active electrodes. If the overall current value is I milliamps (mA), the active electrodes present a total impedance of $R_T$ ohms, and a particular electrode in the group of active electrodes has an impedance value of $R_X$ ohms, then the current distribution value to the particular electrode is $I*R_T/R_X$ milliamps.

Given the current distribution values for each of the active electrodes, the k-means clustering algorithm defines a number of clusters of mean current distribution values. In some examples, the number of clusters may be defined by the number of available stimulation sources, i.e., the number of stimulation sources available or selected for use to deliver stimulation current to the active electrodes. If there are two available stimulation sources, for example, then there are two clusters defined for the k-means clustering algorithm, such that each stimulation source is allocated to one of the electrode clusters.

Although k-means clustering is described as an example of an algorithm that may be used to cluster electrodes based on electrode impedance values for allocation of stimulation sources, other algorithms may be used. For example, other algorithms such as distribution-based clustering, density-based clustering or hierarchical clustering algorithms may be used to generate clusters of electrodes based on impedance values of the electrodes, e.g., either directly or based on simulated current distribution values that are determined for the electrodes based on the impedance values.

As a further example, a sorting algorithm may be used as a clustering algorithm to generate clusters of electrodes. For example, a sorting algorithm may be used to sort electrodes into clusters based on impedance values, or based on current distribution values determined based on impedance values. In particular, a sorting algorithm may be configured to sort electrodes from highest impedance to lowest impedance, or lowest current value to highest current value, and assign the electrodes to clusters based on rank. For example, a group of electrodes with lowest current values (or highest impedance values) may be placed in a first cluster, a group of electrodes with next lowest current values (or next highest impedance values) may be placed in a second cluster, and so forth. The clusters generated by the sorting algorithm may have the same size, i.e., the same number of electrodes, or some clusters may have different sizes. The sizes of clusters may be fixed and predetermined, e.g., based on the number of active electrodes and/or a number of available stimulation sources. In some examples, a smaller cluster size could be set for a cluster of higher impedance (or lower current value) electrodes relative to a larger cluster size for one or more clusters of lower impedance (or higher current value) electrodes.

More sophisticated algorithms could be used for defining the number of clusters in order to, e.g., minimize power consumption. For example, an algorithm may consider internal power consumption of the IPG, which may change along with the number of stimulation sources that are used to deliver stimulation to the electrode clusters. For example, an individual stimulation source may produce power consumption that is increased when multiple stimulation sources are used. An algorithm, such as a k-means clustering algorithm or other clustering algorithms, may take this power consumption into consideration when determining a number of clusters to be generated. For example, if the number of stimulation sources needed for the clusters produces power consumption that exceeds a desired threshold, then it may be desirable to reduce or limit the number of clusters generated by the clustering process, and hence reduce the number of stimulation sources and the amount of power consumption to a level below the threshold.

Upon establishing electrodes in each cluster, the stimulation amplitude delivered to the electrodes in each cluster is determined. Stimulation amplitude of each cluster can be defined in various ways. In one example, the amplitude of each stimulation source may be defined by keeping the amount of current delivered by each electrode in the cluster substantially equal to the amount of stimulation delivered by each electrode in the group of active electrodes. As an illustration, if the total current to be delivered by the group of active electrodes is 2.0 mA and there are sixteen active electrodes, the average current delivered per electrode is 0.125 mA, where average refers to an arithmetic mean. Average and mean may be used interchangeably in this disclosure.

Assume that the k-means clustering algorithm produces, from the sixteen active electrodes, a first cluster of four electrodes and a second cluster of twelve electrodes. For a first cluster with four electrodes, Cluster 1, the amplitude is 0.5 mA, while for the second cluster with twelve electrodes, Cluster 2, the amplitude is 1.5 mA. The total amplitude delivered via both clusters is the desired amplitude of 2.0 mA. The average per-electrode current value for the first cluster is 0.5 mA/4, which is equal to 0.125 mA. The average per-electrode current value for the second cluster is 1.5 mA/12, which is also equal to 0.125 mA. Likewise, the average per-electrode current value for the group of 16 active electrodes is 2.0 mA/16, which is equal to 0.125 mA.

After the clusters of electrodes and stimulation amplitudes have been defined, another simulation of the distribution of the electrical currents among the electrodes may be performed. The result of that current distribution simulation yields current distribution values that may again be used as input to a k-means clustering algorithm for defining clusters of electrodes and stimulation amplitudes in an iterative fashion. In this process, electrodes are binned into one of two or more clusters having a mean current distribution value that is nearest to the current distribution value of the respective electrode. This process may be repeated iteratively, e.g., for a predetermined number of iterations or until the algorithm converges to a point that assignments of electrodes among clusters no longer change.

As described in this disclosure, in some examples, a method for delivering electrical stimulation to a patient via a plurality of implantable electrodes of an IMD may comprise delivering a first portion of the electrical stimulation from a first electrical stimulation source of the IMD via a first cluster of one or more electrodes selected based on impedance values of the one or more electrodes in the first cluster, and delivering a second portion of the electrical stimulation from a second electrical stimulation source of the IMD via a second cluster of one or more electrodes selected based on impedance values of the one or more electrodes in the second cluster.

The electrodes in the first cluster, in this example, are in a group of the plurality of implantable electrodes selected for delivery of the electrical stimulation and comprise less than all of the electrodes in the group. The electrodes in the second cluster are also in the group of the plurality of implantable electrodes selected for delivery of the electrical stimulation. The second cluster is different than the first cluster of one or more electrodes, and comprises less than all of the electrodes in the group. The method may further comprise selecting the group, selecting the first cluster based on impedance values of the one or more electrodes in the first cluster, and selecting the second cluster based on impedance values of the one or more electrodes in the second cluster. The method also may comprise selecting amplitudes for the first and second portions of the electrical stimulation.

A method, in accordance with this example, may be performed by an IMD, e.g., by one or more processors of an IMD, or with a system comprising an IMD and an external programmer, e.g., by a combination of one or more processors of the IMD and one or more processors of the external programmer.

FIG. 1 is a conceptual diagram illustrating an example system including an IMD 100 configured to deliver electrical deep brain stimulation (DBS) therapy to a patient 112 in accordance with the disclosure. In the example of FIG. 1, IMD 100 includes an implantable pulse generator (IPG) 106, lead extension 110, lead 114, electrodes 116 and lead coupling device 118. Lead coupling device 118 may interconnect electrical contacts on lead extension 110 and electrical contacts on lead 114 and may be mountable in a burr hole formed in cranium 122.

IPG 106 may include two or more stimulation sources configured to deliver electrical stimulation to selected electrodes 116 via electrical conductors, within lead extension 110 and lead 114, extending between IPG 106 and electrodes 116. Components of IPG 106 may be contained with a housing, or case, formed from a biocompatible material such as titanium. Although FIG. 1 shows a single lead 114, electrodes 116 may be carried by multiple implantable leads. Accordingly, impedance-based allocation techniques described in this disclosure may be applied to electrodes on a single implantable lead or electrodes distributed across two or more implantable leads, which may be used together to deliver electrical stimulation to patient 112.

The electrical stimulation may be electrical stimulation pulses defined according to one or more parameters, such as voltage or current pulse amplitude, pulse width, and frequency, and may be directed to a desired electrode configuration (e.g., with selected electrodes and polarities). In some examples, IPG 106 may include controlled voltage stimulation sources that generate and deliver stimulation pulses at regulated voltage amplitudes, or controlled current stimulation sources that generate and deliver stimulation pulses at regulated current amplitudes. In general, this disclosure will refer to stimulation sources that deliver stimulation pulses with regulated current amplitudes for illustration. In other examples, instead of pulsed waveforms, stimulation sources of IPG 106 may generate and deliver continuous stimulation waveforms with regulated voltage or regulated current amplitudes.

In the example of FIG. 1, the electrical stimulation therapy is DBS therapy that is delivered by IMD 100 to the brain 120 of patient 112. In some examples, parameters of the stimulation therapy, such as active electrodes, amplitudes, pulse width, and pulse rate, may be selected for DBS so as to reduce or suppress one or more symptoms of a brain disease or disorder, such as symptoms of movement disorders, neurodegenerative impairment, mood disorders or seizure disorders. A movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease or essential tremor. However, the movement disorder may be attributable to other patient conditions. An example of a seizure disorder is epilepsy. Examples of mood disorders include major depressive disorder (MDD), bipolar disorder, anxiety disorders, post-traumatic stress disorder, dysthymic disorder, and obsessive-compulsive disorder (OCD). As described herein, "reducing" or "suppressing" the symptoms of a disorder of the patient 112 may refer to alleviating, in whole or in part, the severity of one or more symptoms of the patient.

Patient 112 ordinarily is a human patient. In some cases, however, IMD 100 may be applied to other mammalian or non-mammalian, non-human patients. As shown in FIG. 1, IMD 100 includes IPG 106, lead extension 110, and lead 114 with electrodes 116. In this example, IMD 100 includes a single lead 114. In other examples, IMD 100 may include two or more leads, including leads implanted in right and left hemispheres of the brain or two leads in the same hemisphere of the brain, in which case two lead extensions may be provided, one for each lead, or lead extension 110 may be bifurcated to provide one branch for each lead. In some examples, IMD 100 includes two IPGs, with each IPG coupled to one of two leads located, respectively, in the right and left hemispheres of the brain.

IPG 106 may electrically couple stimulation sources to selected electrodes 116 via a switch device (not shown in FIG. 1). In some examples, the switch device may be housed within IPG 106. In this example, lead coupling device 118 may be a passive device that connects lead extension 110 to lead 114 or provides a conduit for connection of the lead extension to the lead. In other examples, a switch device may be housed within lead coupling device 118 in a burr hole in cranium 122, making the lead coupling device an active sub-component of IMD 100 that actively connects stimulation sources to selected electrodes 116. In yet other examples, the switch device may reside in a housing that is positioned in a recess formed in cranium 122 that is spaced apart from the burr hole, or the switch device may be carried on a portion of lead 114 that is either within the cranium 122 of patient 112 or external to the cranium and under the scalp of the patient. In other examples, different portions of the switch device may be housed within IPG 106 and lead coupling device 118.

In the example shown in FIG. 1, electrodes 116 of lead 114 are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116 also may be positioned to sense neurological brain signals within brain 120 of patient 112. In some examples, some of electrodes 116 may be configured to sense neurological brain signals and other electrodes 116 may be configured to deliver electrical stimulation to brain 120. In other examples, all of electrodes 116 are configured to both sense neurological brain signals and deliver electrical stimulation to brain 120, e.g., on a selective basis.

IPG 106 includes electrical therapy circuitry that may include stimulation source circuitry, processing circuitry or other electrical circuitry configured to perform the functions attributed to IPG 106. In particular, the therapy circuitry may include two or more stimulation sources configured to generate and deliver electrical stimulation therapy to patient 112 via a selected group of active electrodes 116 of lead 114. The group of active electrodes 116 that is selected to deliver electrical stimulation to patient 112, and, in some cases, the polarity or polarities of the active electrodes, may also be referred to as a stimulation electrode combination. The stimulation electrode combination can be selected for a particular patient 112 and target tissue site (e.g., selected based on the patient condition).

The group of active electrodes may include all or less than all of electrodes 116. Electrodes 116 may be arranged as ring electrodes at different axial positions along lead 114. Another type of lead is a so-called paddle lead, which includes electrodes typically arranged in a two-dimensional array. Alternatively, electrodes 116 may have a complex electrode geometry such that electrodes are located at different axial positions along lead 114 and different circumferential positions around the respective lead. This disclosure will generally refer to electrodes 116 having a complex electrode geometry. By distributing electrodes at various positions along the axial length and about the circumference of the lead, a complex electrode array geometry may be useful in producing directional and shaped electrical fields. Electrodes at different circumferential positions may support more directional stimulation, e.g., than ring electrodes, to more precisely target tissue for stimulation and possibly reduce side effects associated with stimulating larger volumes of tissue.

As one example of a complex electrode geometry, electrodes 116 may form an electrode array comprising rings of electrodes at different axial positions along lead 114, where each ring includes two or more separate electrodes at different positions around the circumference of the lead, rather than a full ring electrode. This electrode configuration is sometimes referred to as a segmented electrode array. In one example, at each axial position, a ring of electrodes may include four electrodes at different circumferential positions, which may be spaced such that the centers of the electrodes are approximately 90 degrees from another, forming medial, posterior, lateral and anterior electrodes at each axial position.

The positions of the medial, posterior, lateral and anterior electrodes may be offset, in some examples, between adjacent axial rings on an alternating basis. For example, at a first axial position, the medial, posterior, lateral and anterior electrodes may be centered, respectively, at 0, 90, 180 and 270 degrees. At a second, adjacent axial position, the ring may be offset from the first axial position such that the medial, posterior, lateral and anterior electrodes are centered at 45, 135 and 225, and 315 degrees. At a third axial position on a side of the second axial position opposite the first axial position, the ring of electrodes may be positioned at the same position as the electrodes in the ring at the first axial position. This offset arrangement may continue in an alternating pattern among the various axial rings on lead 114.

Electrodes 116 may be used on a selective basis to sense electrical brain signals. In some examples, neurological signals sensed within brain 120 may reflect changes in electrical current produced by the sum of electrical potential differences across brain tissue. Examples of neurological brain signals include, but are not limited to, electrical signals generated from local field potentials (LFP) sensed within one or more regions of brain 120, such as an electroencephalogram (EEG) signal, or an electrocorticogram (ECoG) signal. Local field potentials, however, may include a broader genus of electrical signals within brain 120. In some examples, the neurological brain signals may be used to select electrodes and set or adjust parameters for delivery of stimulation to particular target tissue sites within brain 120 as the target tissue site for the electrical stimulation.

Target tissue sites for DBS therapy may include tissue sites within anatomical structures such as the thalamus, subthalamic nucleus or globus pallidus of brain 120, as well as other target tissue sites. The specific target tissue sites and/or regions within brain 120 may be selected based on the patient condition, neurological signals sensed by electrodes 116, or other information. In some examples, both a stimulation electrode combination and sense electrode combinations may be selected from the same set of electrodes 116. In other examples, the electrodes used for delivering electrical stimulation may be different than the electrodes used for sensing neurological brain signals.

IPG 106 may be implanted within a subcutaneous pocket above the clavicle, or, alternatively, on or within cranium 122 or at any other suitable site within patient 112. Generally, IPG 106 may have a housing or "case" constructed of a biocompatible material such as, e.g., titanium, that resists corrosion and degradation from bodily fluids. IPG 106 may comprise a hermetic housing to substantially enclose components, such as a processor, therapy module, and memory.

As shown in FIG. 1, implantable lead extension 110 is coupled to IPG 106 via connector 108 (also referred to as a connector block or a header of IPG 106). In the example of FIG. 1, lead extension 110 traverses from the implant site of IPG 106 and along the neck of patient 112 to cranium 122 of patient 112 to access brain 120. In some instances, as when IPG 106 is implanted on or within cranium 122, lead extension 110 may not be needed in the system. In the example shown in FIG. 1, lead 114 is implanted within the right hemisphere of patient 112. Alternatively, lead 114 may be implanted in the left hemisphere of brain 120 of patient 112, or two leads may implanted in the right and left hemispheres, respectively, of the brain. Although IPG 106 is shown coupled to lead 114 via lead extension 110, other configurations are possible. For example, IPG 106 and electrodes 116 could be integrated into a device that is implanted on or within cranium 122.

IMD 100 may communicate wirelessly with an external medical device programmer 104. IMD 100 and external programmer 104 together may form a system for delivery of electrical stimulation therapy. Programmer 104 is an external computing device that the user, e.g., a clinician and/or patient 112, may use to communicate with IPG 106. Programmer 104 may be configured to program one or more parameters of electrical stimulation delivered by IMD 100. For example, programmer 104 may receive user input from a clinician or patient, and permit a clinician or patient to program parameters of IPG 106, adjust parameters of the IPG, retrieve operational information from the IPG and/or retrieve diagnostic information from the IPG. Programmer 104 represents a patient programmer or a clinician programmer. A clinician programmer typically includes more programming features than a patient programmer, such that more complex or sensitive tasks are limited to the clinician programmer to prevent an untrained patient from making undesirable changes to IPG 106.

When programmer 104 is configured for use by the clinician, programmer 104 may be used to transmit programming information to IPG 106. This information may include hardware information, such as the type of leads 114 and the electrode arrangement, the position of leads 114 within brain 120, the configuration of electrode array 116, initial therapy programs defining therapy parameter values, and other information the clinician desires to program into IPG 106. Programmer 104 may also be configured to control IPG 106 to perform functional tests, either automatically or at the direction of a clinician. For example, programmer 104 may control IPG 106 to measure the impedance between individual electrodes 116 and a reference electrode, e.g., a reference electrode on IPG 106, a reference electrode on lead 114, or a reference electrode between IPG 106 and lead 114, and/or the impedance between individual electrodes 116. Measurement of impedance may be performed by IPG 106, under control by programmer 104, during clinic visits to a clinician by a patient or upon remote interrogation and programming by a clinician. Additionally or alternatively, IPG 106 and/or programmer 104 may measure impedance automatically, e.g., at regular or scheduled intervals, and/or in response to sensed events or conditions. Measured impedance values may be used by IPG 106 and/or programmer 104 for electrode clustering and stimulation source allocation as described in various examples of this disclosure.

The clinician may also store therapy programs within IPG 106 with the aid of programmer 104. During a programming session, the clinician may determine one or more therapy programs that may provide efficacious therapy to patient 112 to address symptoms associated with the patient condition. For example, the clinician may select two or more stimulation electrodes with which stimulation is delivered to brain 120. For example, stimulation may be delivered using one or more cathodes and one or more anodes formed by electrodes 116 carried by lead 114, or one or more cathodes formed by electrodes 116 carried by lead 114 and one or more anodes formed by one or more electrodes provided elsewhere, such as on a case of IPG 106, on lead 114 carrying the electrodes 116, or between lead 114 and IPG 106, e.g., on lead coupling device 118. The anode or anodes may form a reference electrode for stimulation and measurement of impedance. In other examples, the reference electrode or electrodes may be cathodes and electrodes 116 may be anodes.

During the programming session, the clinician may evaluate the efficacy of a specific program based on feedback provided by patient 112 or based on one or more physiological parameters of patient 112 (e.g., muscle activity, muscle tone, rigidity, tremor, etc.). Alternatively or additionally, identified patient behavior from video information may be used as feedback during the initial and subsequent programming sessions. Programmer 104 may assist the clinician in the creation/identification of therapy programs by providing a system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IPG 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IPG 106 needs to be replaced or recharged. For example, programmer 104 may include an alert LED, present a message to patient 112 via a programmer display, or generate an audible sound or somatosensory cue to confirm patient input was received, e.g., to indicate a patient state or to manually modify a therapy parameter.

IMD 100 may be implemented to provide chronic stimulation therapy to patient 112 over the course of several months or years. However, stimulation may be employed on a trial basis to evaluate therapy before committing to full implantation. If implemented temporarily, some components of IMD 100 may not be implanted within patient 112. For example, patient 112 may be fitted with an external medical device, such as a trial stimulator, rather than IPG 106. The external medical device may be coupled to percutaneous leads or to implanted leads via a percutaneous extension. If the trial stimulator indicates an IMD 100 would be likely to provide effective treatment to patient 112, the clinician may implant IMD 100 as a chronic stimulator within patient 112 for relatively long-term treatment.

Figure 2:
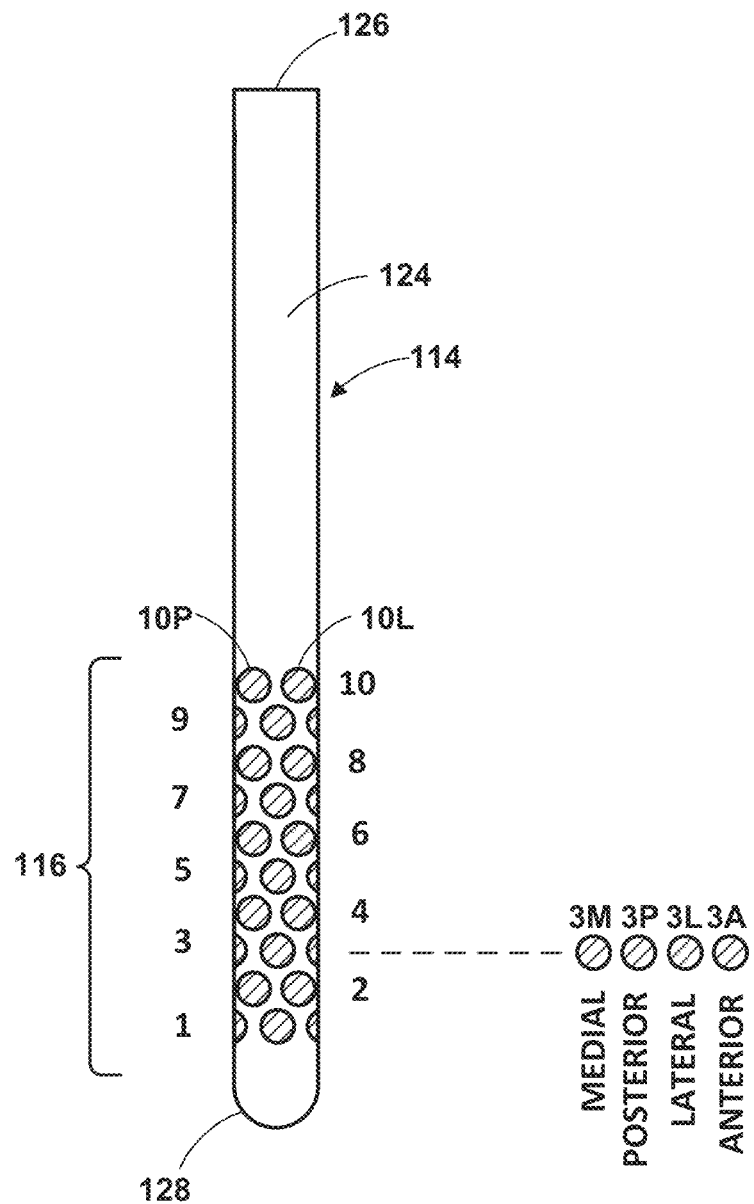
FIG. 2 is a schematic diagram illustrating an implantable DBS lead with an array of electrodes in accordance with an example of the disclosure.

FIG. 2 is a schematic diagram illustrating an example of implantable lead 114 with an array of electrodes 116 in accordance with the disclosure. Lead 114 may be sized appropriately for implantation in brain 120 to deliver DBS therapy to patient 112. As shown in FIG. 2, lead 114 includes electrodes 116, lead body 124, proximal end 126 and distal end 128. Proximal end 126 be coupled to a lead extension, such as lead extension 110, either directly or via a connector or switch device such as lead coupling device 118 within a burr hole. Accordingly, proximal end may include electrical contacts (not shown) coupled, respectively, to individual electrodes 116 via elongated conductors that extend along the length of lead 114. The electrical contacts may be coupled to corresponding electrical contacts of lead extension 110, such that conductors in lead 114, proximal contacts on lead 114, distal contacts on lead extension 110, conductors in lead extension 110, proximal contacts on lead extension 110, and one or more switch devices couple respective electrodes to stimulation sources in IPG 106. Electrodes 116 may be coupled to the stimulation sources via a switch device in IPG 106. Alternatively, electrodes 116 may be coupled to the stimulation sources via a switch device in lead coupling device 118.

Elongated conductors in lead extension 110 may be, for example, coiled or axial conductors that connect at the proximal end, directly or indirectly, to either stimulation sources or a switch device in IPG 106 and connect at the distal end, directly or indirectly, to either electrical contacts of lead 114 or a switch device in lead coupling device 118. Alternatively, the switch device may be located in a housing positioned on the skull a distance apart from the burr hole. The switch device may be implemented as a flex circuit or other suitable circuit that can be carried by a body of lead 114 or lead extension 110, or positioned somewhere else in the system. Elongated conductors may be formed in or on lead 114 and extend between proximal contacts on the lead and electrodes 116. There may be a one-to-one connection, provided by the elongated conductors, between proximal contacts on lead 114 and electrodes 116, so that electrodes can be individually selected for delivery of electrical stimulation.

In some examples, lead 114 may be constructed with a carrier and a thin film (not shown), e.g., as described in U.S. Patent Application Publication No. 2016/0144189, to Bakker et al. The carrier may be sized and shaped to provide the mechanical configuration of DBS lead 114. The thin film may be wrapped around the circumference of the carrier (e.g., in a helical pattern) and include electrically conductive electrodes, electrically conductive proximal contacts, and electrically conductive traces (i.e., forming elongated conductors) extending between the electrodes and the contacts. In this example, the electrodes, contacts and conductors may be formed in desired patterns on the thin film, for example, by deposition, etching, printing or the like and the thin film may be wrapped around the carrier to form lead 114.

Lead 114 may include any number of electrodes, contacts and conductors. In the example of FIG. 2, lead 114 includes the rings of electrodes at axial positions 1-10, where axial position 1 is most distal and axial position 10 is most proximal. The ring at each axial position includes 4 electrodes, at respective medial, posterior, lateral and anterior circumferential positions, which may be approximately 90 degrees apart from one another. For example, at axial position 3, the respective ring includes electrodes 3M (medial), 3P (posterior), 3L (lateral), and 3A (anterior), shown in FIG. 2 as if the entire circumference of lead 114 were visible. At axial position 10, electrodes 10P (posterior) and 10L (lateral) are shown. As described above, the positions of the medial, posterior, lateral and anterior electrodes may be offset, in some examples, between adjacent axial rings on an alternating basis.

In the example of lead 114 in FIG. 2, there are ten axial rings, each with four electrodes 116, amounting to 40 electrodes. In other examples, there may be more or less electrodes per ring at each axial position, more rings at more axial positions, less rings at less axial positions, and so forth. The number of electrodes may be sufficient to permit directionality, location, sizing and shaping of a stimulation field relative to a desired target, such as an anatomical structure within the brain. Accordingly, the number of electrodes on lead 114 may be greater than or equal to 8 electrodes, greater than or equal to 16 electrodes, greater than or equal to 32 electrodes, or greater than or equal to 40 electrodes. There may be more, or many more, electrodes than available stimulation sources in IPG 106. Also, in some examples, electrodes 116 may be provided on a single lead 114 or on multiple leads coupled to IPG 106.

Figure 3A:
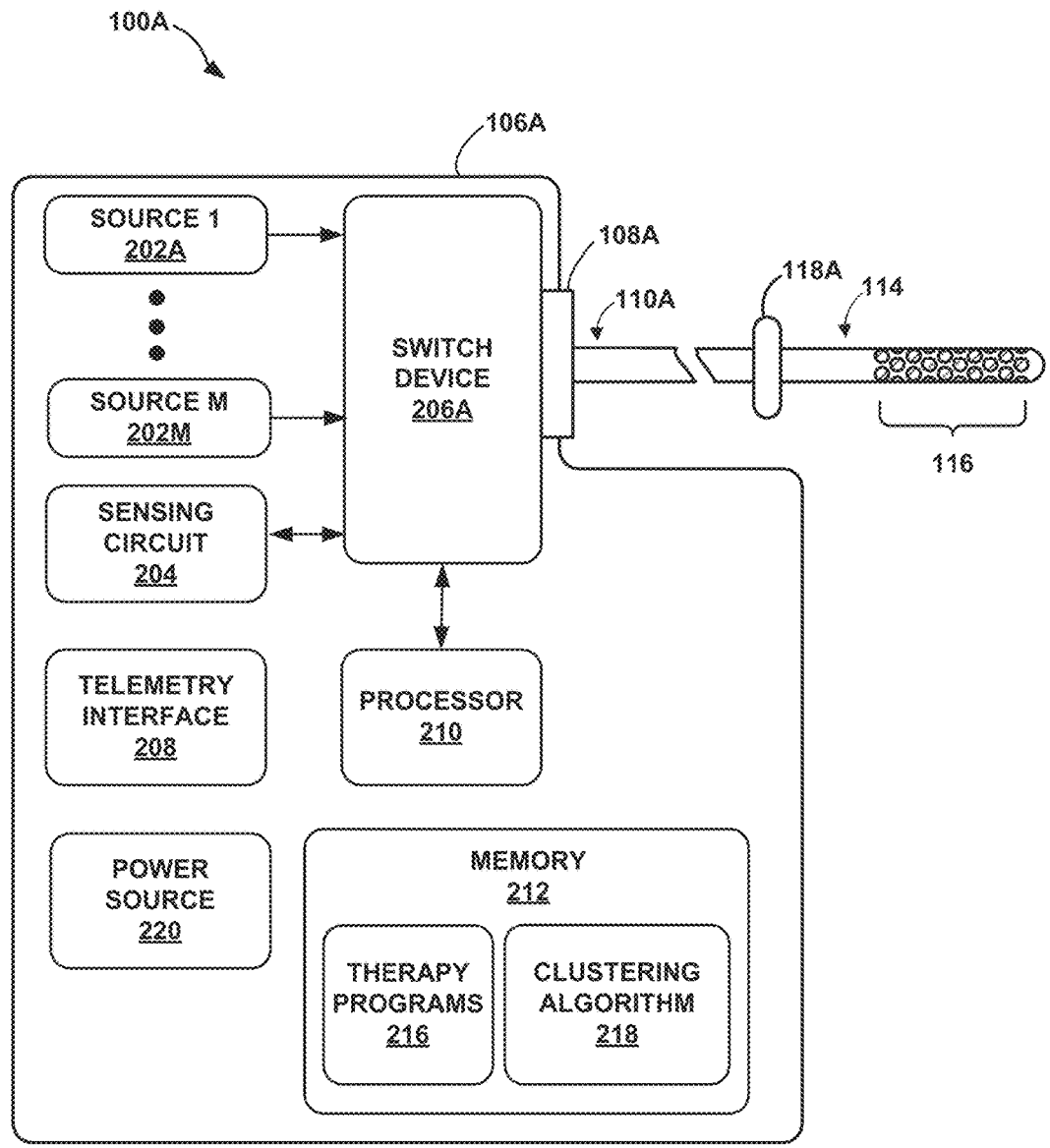
FIG. 3A is a block diagram illustrating an IMD for delivering DBS therapy in accordance with an example of the disclosure.
Figure 3B:
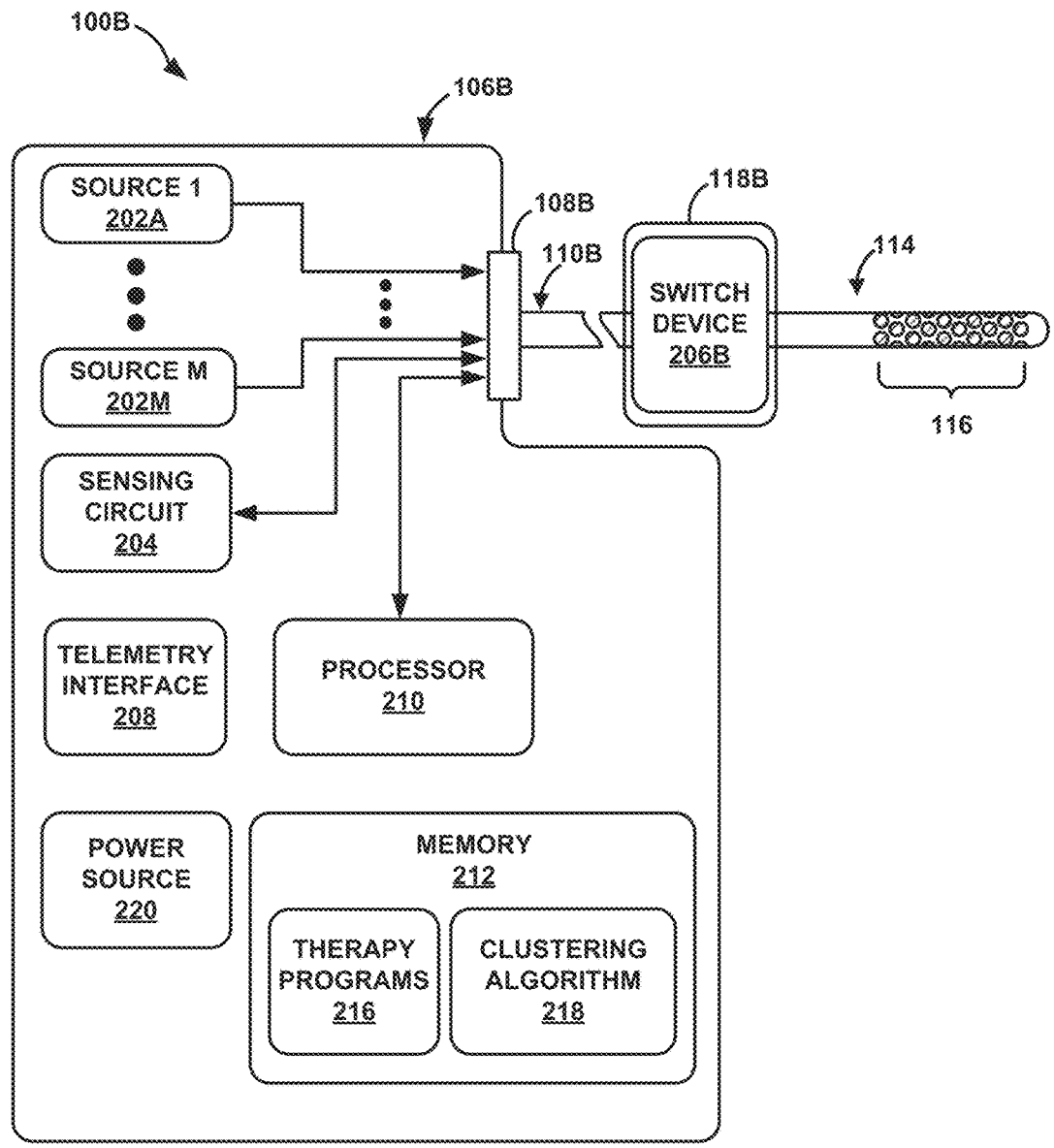
FIG. 3B is a block diagram illustrating another example of an IMD for delivering DBS therapy in accordance with the disclosure.

FIG. 3A is a block diagram illustrating an example of an IMD 100A for delivering DBS therapy in accordance with the disclosure. FIG. 3B is a block diagram illustrating another example of an IMD 100B for delivering DBS therapy in accordance with the disclosure. IMD 100A and 100B correspond to IMD 100 of FIG. 1. FIGS. 3A and 3B illustrate additional example features of IMD 100 of FIG. 1. In the examples shown in both FIG. 3A and FIG. 3B, IPG 106A and IPG 106B of IMD 100A, 100B, respectively, include processor 210 and memory 212, stimulation sources 202A-202M (collectively 202), sensing circuit 204, telemetry interface 208, switch device 206A (in IPG 106A of FIG. 3A) or 206B (in IPG 106B of FIG. 3B), connector 108A or 108B, and power source 220.

Each of these components may include electrical circuitry configured to perform the functions attributed to each respective components. For example, processor 210 may include processing circuitry, sensing circuit 204 may include sensing circuitry, and telemetry interface 208 may include wireless telemetry circuitry. Processor 210 may comprise one or more processors configured to perform a variety of operations described in this disclosure. Memory 212 may include any volatile or non-volatile media, such as a random access memory (RAM), read only memory (ROM), non-volatile RAM (NVRAM), electrically erasable programmable ROM (EEPROM), flash memory, and the like. Memory 212 may store computer-readable instructions that, when executed by processor 210, cause IPG 106 to perform various functions.

In the example of FIG. 3A, switch device 206A is provided within IPG 106A and is configured to selectively couple each of stimulation sources 202 to respective electrodes 116 of lead 114, e.g., via connector 108A and contacts and conductors associated with lead extension 110A and lead 114. Each stimulation source 202 may be a controlled current source having electrical circuitry configured to deliver regulated current signals, including regulated current pulses, as electrical stimulation with desired current amplitudes, pulse widths and pulse rates. Alternatively, stimulation source 202 may be a controlled voltage source having electrical circuitry configured to deliver regulated voltage signals, including regulated voltage pulses, as electrical stimulation with desired voltage amplitudes, pulse widths and pulse rates.

Although stimulation source 202 is referred to as a source, in various examples, stimulation source 202 may be configured to operate as a current source or sink. For example, stimulation source 202 may be configured to operate as a current source that generates cathodic or anodic current. For example, stimulation source 202 may source 2 milliamps of current or, in another example, sink 2 milliamps of current. In general, stimulation source 202 is configured to generate the electrical stimulation, e.g., in the form of stimulation current or stimulation voltage, that is delivered to patient 112 for electrical stimulation therapy, such as DBS therapy. Generation of cathodic current by stimulation sources 202 will be described for purposes of illustration.

Conductors in lead extension 110A and conductors in lead 114 may be coupled to one another by lead coupling device 118A. In the example of FIG. 3B, switch device 206B is provided in lead coupling device 118B and is configured to selectively couple each of stimulation sources 202 to respective electrodes 116 of lead 114, e.g., via contacts and conductors associated with lead extension 110 and lead 114, and via a connector 108B formed in IPG 106B. In each case, switch device 206A, 206B may include switch circuitry (e.g., a crosspoint switch matrix or other type of switch circuitry or switch matrix) that may be controlled by processor 210 to connect particular stimulation sources 202 to selected electrodes 116. For example, switch device 206A, 206B may couple a first stimulation source 202 to electrodes 116 in a first cluster of electrodes of a group of active electrodes used to deliver stimulation, and couple a second stimulation source 202 to electrodes 116 in a second cluster of electrodes of the group of active electrodes used to deliver stimulation. Each of the clusters may have one, two, or more electrodes depending on the outcome of impedance-based allocation of electrodes into the clusters.

Switch device 206A, 206B may be coupled to multiple (i.e., two or more) stimulation sources 202, sensing circuit 204 and processor 210 (via connector 108B in the case of switch device 206B, which is external to IPG 106B). Processor 210 may transmit control signals to switch device 206A, 206B to cause switch device 206A, 206B to connect electrodes 116 to stimulation sources 202A, 202B for delivery of stimulation. Processor 210 may transmit control signals to switch device 206A, 206B to cause switch device 206A, 206B to connect electrodes to sensing circuit 204 for impedance measurements. In particular, sensing circuit 204 may be coupled to electrodes 116 via switch device 206A, 206B to measure impedance between individual electrodes 116 and a reference electrode or reference electrodes carried by lead 114, carried by IPG 106A, 106B, carried by a component coupled between the lead and IPG, such as lead coupling device 118, or provided elsewhere in IMD 100A, 100B.

For example, the reference electrode, which also may be referred to as a ground or return electrode, may be formed on a case of IPG 106A, 106B, formed by a particular electrode formed on lead 114, e.g., as a contact, ring, or coil, and dedicated to serve as a reference electrode, formed by one of the electrodes 116 on lead 114 on a selective basis, e.g., by switching to couple a ground node of one or more stimulation sources 202 to one or more electrodes 116 selected to serve as a reference electrode to provide a return path, formed by a particular electrode on lead coupling device 118, coupled between IPG 106A, 106B and lead 114, or formed by a component elsewhere in IMD 100A, 100B.

As examples, a reference electrode may be formed as a dedicated reference electrode on IPG 106A, 106B, on lead 114 or on lead coupling device 118, or the reference electrode may be provided by selective switching by switch device 206A, 206B to couple one or more of the electrodes 116 to a ground node of stimulation sources 202 to serve as a reference electrode. In each case, the respective reference electrode or multiple reference electrodes may be coupled to a ground node of stimulation sources 202 to provide a return path for stimulation delivered by active electrodes 116. In some examples, it may be sufficient to form the reference electrode on IPG 106A, 106B to provide a return path to a point that is relatively remote from electrodes 116. In other examples, it may be desirable to position the reference electrode more closely to electrodes 116, providing a shorter return path, e.g., by forming the reference electrode on lead 114 or lead coupling device 118, or selectively using one or more of electrodes 116 on lead 114 as the reference electrode.

Sensing circuit 204 also may be coupled to electrodes 116 via switch device 206A, 206B to measure impedance between individual electrodes and other electrodes of lead 114. Sensing circuit 204 may measure impedance values for all electrodes 116 or impedance values for electrodes in a group of active electrodes, which may be less than all of the electrodes carried by lead 114. Sensing circuit 204 may measure impedance values between electrodes 116 and a reference electrode, which may be the same electrode used as return electrode for stimulation. Switch device 206A, 206B may couple stimulation sources 202 and sensing circuit 204 to electrodes 116 using the same conductors. In particular, conductors extending along lead 114 may be used for both delivery of stimulation and impedance sensing, e.g., at different times.

Processor 210 may use the impedance values measured by sensing circuit 204 to control switch device 206A, 206B and stimulation sources 202 to provide impedance-based allocation of stimulation sources and stimulation amplitudes to clusters of electrodes 116. In particular, processor 210 assigns implantable electrodes 116, in a group of active electrodes, to clusters based on impedance values of the electrodes, couples the electrodes in the electrode clusters to respective stimulation sources 202, and controls the stimulation sources to generate respective stimulation amplitudes for the electrode clusters. In some examples, processor 210 may perform a clustering algorithm to select the clusters. In other examples, processor 210 may select the clusters based on information indicating clusters selected by external programmer 104.

Processor 210 may control switch device 206A, 206B to cluster electrodes 116 having relatively similar impedance values, such that electrodes in each cluster present less variation in impedance relative to impedance variation across the group of electrodes. Processor 210 may couple stimulation sources 202 to the clusters, and control the stimulation amplitudes produced by the stimulation sources for each cluster, so that variation in current outflow through electrodes in the clusters may be reduced, promoting more uniform distribution of stimulation current across the group of active electrodes and a more uniform stimulation field.

In the examples of FIGS. 3A and 3B, memory 212 stores instructions and data associated with therapy programs 216 and clustering algorithm 218. Therapy programs 216 and clustering algorithm 218 may be stored in separate memories within memory 212 or separate areas within memory 212. Each stored therapy program 216 may define a particular set of electrical stimulation parameters (e.g., a therapy parameter set), such as a stimulation electrode combination, electrode polarity, current or voltage amplitude, pulse width, and pulse rate.

In some examples, individual therapy programs may be stored as a therapy group, which defines a set of therapy programs defining stimulation that may be delivered together, e.g., simultaneously or on a time-interleaved basis. A therapy program may indicate selected electrodes in a group of active electrodes for delivery of stimulation, with current pulse amplitude, pulse width and pulse rate (i.e., pulse frequency) of the stimulation to be delivered via the selected electrodes.

Processor 210 may use the clustering algorithm 218 to cluster the selected electrodes based on impedance values measured by sensing circuit 204 for impedance-based allocation of stimulation. Some of the operations performed by processor 210 for impedance-based allocation of stimulation may be performed by or in coordination with one or more processors associated with programmer 104. Accordingly, although impedance-based allocation processing operations may be described in this disclosure with respect to processor 210, it should be understood that some or all of such processing operations may be performed by processor 210 alone, by processor 210 in coordination with one of more processors of programmer 104, by processor 310 under control of one or more processors of programmer 104, by one or more processors of programmer 104, or by or in coordination with one or more other processors.

Processor 210 may control sensing circuit 204 to obtain the impedance values for electrodes 116 at the time of implantation and/or activation of IMD 100A, 100B, e.g., prior to commencing delivery of stimulation. These impedance values may be used by processor 210 to execute the clustering algorithm when a therapy program 216 is activated or modified. For example, if a therapy program is activated or modified, resulting in a change in the group of active electrodes selected for stimulation, processor 210 may use the measured impedance values of the currently selected electrodes in the clustering algorithm. Hence, processor 210 may re-run the clustering algorithm with the previously measured impedance values when the selected electrodes change. Alternatively, or additionally, processor 210 may re-run the clustering algorithm during clinic visits by a patient, upon remote interrogation and programming by a clinician, at regular or scheduled intervals, and/or in response to sensed events or conditions. Also, instead of using pre-measured impedance values obtained prior to activation, processor 210 may control sensing circuit 204 to obtain new impedance measurements for electrodes 116 at any of the times mentioned above. As a further example, the clustering algorithm or some aspects of the clustering algorithm may be performed by one or more processors of external programmer 104, alone or in conjunction with processor 210.

Electrical stimulation generated by stimulation sources 202 may have one or more parameters selected to reduce or suppress one or more symptoms of a brain disease or disorder, such as symptoms of movement disorders, neurodegenerative impairment, mood disorders or seizure disorders. In one example, for managing a movement disorder of a patient, such as Parkinson's Disease or essential tremor, processor 210 may control stimulation sources 202 to generate DBS therapy with the following stimulation parameters: Pulse Rate: from approximately 100 Hertz to approximately 185 Hertz, such as from approximately 130 to 150 Hertz; Current Pulse Amplitude (in the case of a regulated current controlled source): from approximately 1.5 milliamps to approximately 5.0 milliamps, such as from approximately 2.0 milliamps to approximately 3.0 milliamps; Voltage Pulse Amplitude (in the case of a regulated voltage controlled stimulation source): from approximately 1.5 volts to approximately 5.0 volts, such as from approximately 2.0 volts to approximately 3.0 volts; Pulse Width: from approximately 60 microseconds to approximately 120 microseconds, such as from approximately 60 microseconds to approximately 90 microseconds.

In another example, for managing obsessive compulsive disorder (OCD), processor 210 may control stimulation sources 202 to generate DBS therapy with the following stimulation parameters: Pulse Rate: from approximately 100 Hertz to approximately 185 Hertz, such as from approximately 130 to 150 Hertz; Current Pulse Amplitude (in the case of a regulated current controlled source): from approximately 3.0 milliamps to approximately 7.0 milliamps, such as from approximately 4.5 milliamps to approximately 6.0 milliamps; Voltage Pulse Amplitude (in the case of a regulated voltage controlled stimulation source): from approximately 3.0 volts to approximately 7.0 volts, such as from approximately 4.5 volts to approximately 6.0 volts; Pulse Width: from approximately 60 microseconds to approximately 300 microseconds, such as from approximately 90 microseconds to approximately 140 microseconds. The above parameters for Parkinson's Disease or essential tremor, and for OCD, are examples, and may vary, e.g., according to different diseases, disorders, symptoms, anatomical targets or the like.

Accordingly, in some examples, stimulation sources 202 may generate electrical stimulation pulses in accordance with the electrical stimulation parameters noted above. In some examples, a desired pulse amplitude of the DBS therapy may be divided between a first portion of the pulse amplitude delivered by a first stimulation source 202 to a first cluster of electrodes 116 and a second portion of the pulse amplitude delivered by a second stimulation source to a second cluster of electrodes, where the sum of the first and second portions is substantially equal to the desired pulse amplitude of the DBS therapy. Again, each cluster may have one, two, or more electrodes depending on the result of impedance-based allocation of the electrodes to the clusters. While stimulation pulses are described, stimulation signals may take other forms, such as continuous-time waveforms (e.g., sine waves) or the like.

Processor 210 (and/or processor 302 of external programmer 104 in FIG. 4) may include one or more processors comprising fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein, and may be embodied as firmware, hardware, software or any combination thereof. Processor 302 (FIG. 4) associated with programmer 104 may be constructed from circuitry similar to that of processor 210. Processor 210 may control stimulation sources 202 according to therapy programs 216 stored in memory 212 to apply particular stimulation parameter values specified by one or more of the programs, such as amplitude, pulse width, and pulse rate.

In the examples shown in FIGS. 3A and 3B, processor 210 also controls switch device 206A, 206B to apply the stimulation signals generated by stimulation sources 202 to selected clusters of electrodes 116. In particular, switch device 206A, 206B may couple stimulation signals to selected conductors within lead 114 (and lead extension 110 in FIG. 3A), which, in turn, deliver the stimulation across selected electrodes 116. Switch device 206 may be a switch array, crosspoint switch matrix, multiplexer, or any other type of switching circuitry configured to selectively couple stimulation energy from stimulation sources 202 to selected electrodes 116 and to selectively couple sensing circuit 204 to selected electrodes 116 to sense impedance values and/or bioelectrical brain signals.

Telemetry interface 208 may include electrical circuitry that supports wireless communication between IMD 100A or 100B and an external programmer 104 or another computing device under the control of processor 210. Processor 210 of IMD 100A or 100B may receive, as updates to programs, values for various stimulation parameters such as amplitude and electrode combination, from programmer 104 via telemetry interface 208. The updates to the therapy programs may be stored within therapy programs 216 of memory 212. Telemetry interface 208 in IMD 100A or 100B, as well as telemetry interfaces in other devices and systems described herein, such as programmer 104, may accomplish communication by radiofrequency (RF) communication techniques. In addition, telemetry interface 208 may communicate with external medical device programmer 104 via proximal inductive interaction of IMD 100A or 100B with programmer 104. Telemetry interface 208 may send information to external programmer 104 on a continuous basis, at periodic intervals, or upon request from IMD 100A or 100B or programmer 104.

Power source 220 delivers operating power to various components of IPG 106A, 106B. Power source 220 may include a small rechargeable or non-rechargeable battery and a power generation circuit to produce the operating power. Recharging may be accomplished through proximal inductive interaction between an external charger and an inductive charging coil within IPG 106A, 106B. In some examples, power requirements may be small enough to allow IPG 106A, 106B to utilize patient motion and implement a kinetic energy-scavenging device to trickle charge a rechargeable battery. In other examples, traditional, nonrechargeable batteries may be used for a limited period of time.

Figure 4:
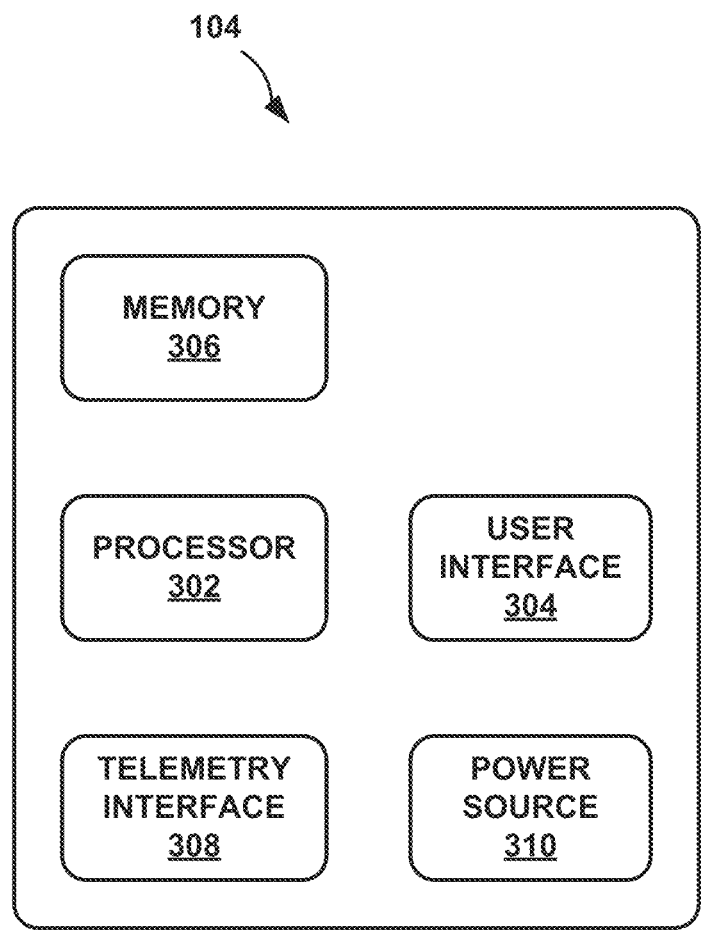
FIG. 4 is a block diagram illustrating an external programmer of FIG. 1 for programming an IMD in accordance with an example of the disclosure.

FIG. 4 is a block diagram of external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include a processor 302, user interface 304, memory 306, telemetry interface 308, and power source 310. Memory 306 may store instructions that, when executed by processor 302, cause processor 302 and external programmer 104 to provide the functionality ascribed to external programmer 104 throughout this disclosure. Each of these components, or modules, may include electrical circuitry that is configured to perform some or all of the functionality described herein. For example, processor 302 may include processing circuitry, similar to processing circuitry of processor 210, configured to perform the processes discussed with respect to processor 302.

In general, programmer 104 comprises any suitable arrangement of hardware, alone or in combination with software and/or firmware, to perform the techniques attributed to programmer 104, and processor 302, user interface 304, and telemetry interface 308 of programmer 104. In various examples, processor 302 of programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Memory 306 may be formed by any of a variety of devices such as those described above with respect to memory 212 of IPG 106A, 106B. Likewise, processor 302 may be formed by any of a variety of processing circuitry such as the circuitry described above with respect to processor 210 of IPG 106A, 106B. Various aspects of methods for impedance-based clustering of electrodes, as described in this disclosure, may be performed by processor 210, processor 302, or by processor 210 and processor 302.

User interface 304 may include a button or keypad, lights, a speaker for voice commands, a display, such as a liquid crystal (LCD), light-emitting diode (LED), or organic light-emitting diode (OLED). In some examples the display may be a touch screen. User interface 304 may be configured to display any information related to the delivery of stimulation therapy, identified patient behaviors, sensed patient parameter values, patient behavior criteria, or any other such information. User interface 304 may also receive user input. The input may be, for example, in the form of pressing a button on a keypad or selecting an icon from a touch screen.

Telemetry interface 308 may include electrical circuitry to support wireless communication between IPG 106 and programmer 104 under the control of processor 302. Telemetry interface 308 may also be configured to communicate with another computing device via wireless communication techniques, or direct communication through a wired connection. In some examples, telemetry interface 308 provides wireless communication via an RF or proximal inductive medium. In some examples, telemetry interface 308 includes an antenna, which may take on a variety of forms, such as an internal or external antenna.

Figure 5:
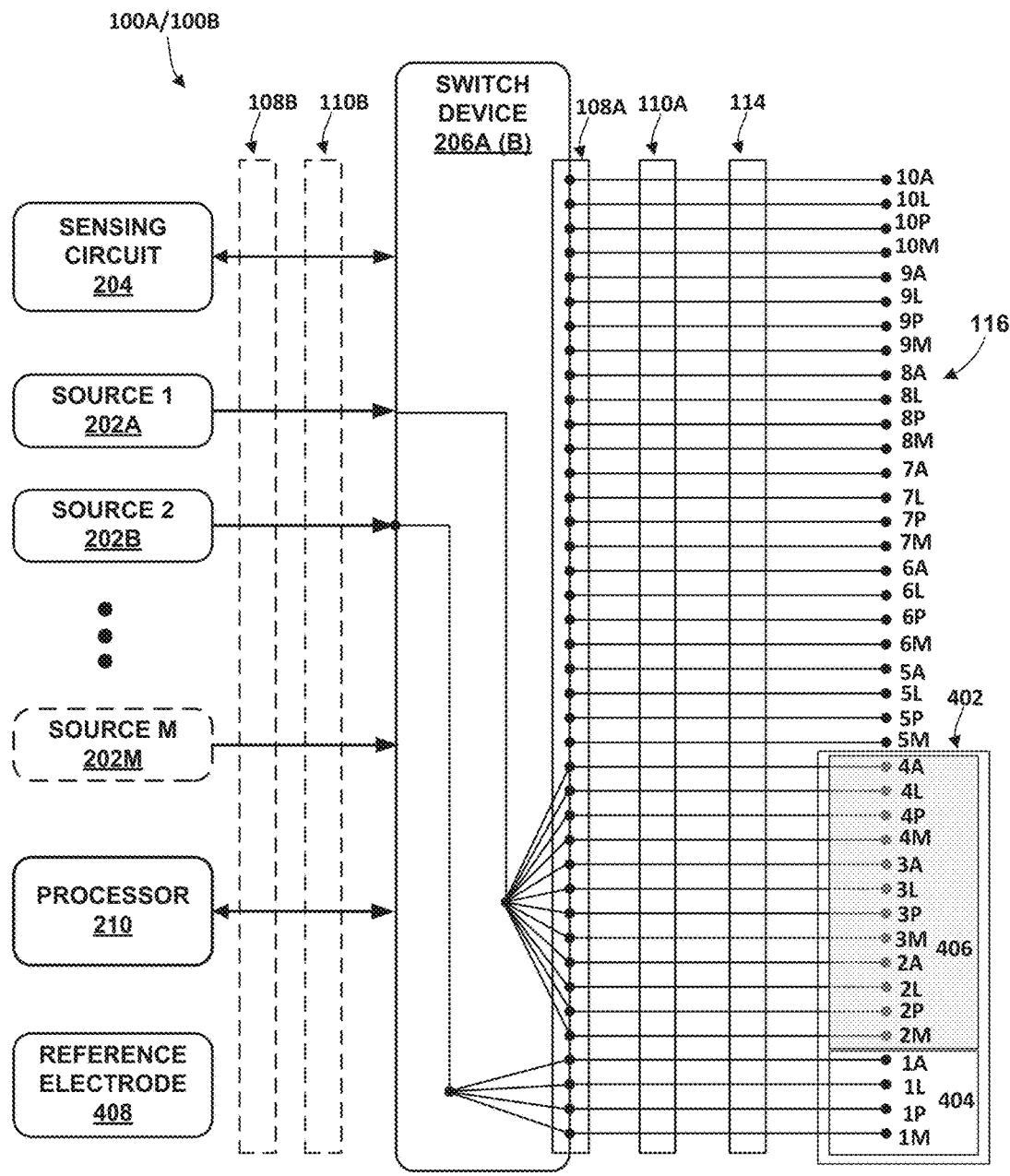
FIG. 5 is a block diagram illustrating impedance-based allocation of stimulation sources to electrode clusters for delivery of DBS therapy by the IMD of FIG. 3A or 3B in accordance with an example of the disclosure.

FIG. 5 is block diagram illustrating an example of impedance-based allocation of stimulation sources 202 to electrode clusters in IMD 100A, 100B via switch device 206A or 206B for delivery of DBS therapy in accordance with the disclosure. In the example of FIG. 5, an output side of switch device 206A or 206B is coupled to electrodes 116 and an input side is coupled to stimulation sources 202, processor 210, and sensing circuit 204. Switch device 206A or 206B couples stimulation sources 202 to selected electrodes 116 to deliver stimulation therapy. Switch device 206A or 206B couples sensing circuit 204 to selected electrodes 116 to measure impedance values for the electrodes, e.g., relative to a reference electrode 408 on IPG 106A or 106B, on lead 114, and/or on a component coupled between the lead and IPG, such as lead coupling device 118, and/or elsewhere within IMD 100A, 100B, to support impedance-based allocation of stimulation in accordance with this disclosure. In some cases, there may be more than one electrode selected as the reference electrode, and the reference electrodes may be in different locations. For instance, one reference electrode may be located on a housing of IPG 106 and another reference electrode may be carried by lead 114. Alternatively, for an IMD comprising two IPGs, one reference electrode may be located on a housing of a first IPG and another reference electrode may be located on a housing of a second IPG. In still another example, one reference electrode may be located on a first lead and another reference electrode may be located on a second, different lead. In some examples, conductors within lead extension 110A and lead 114 may be shared by stimulation sources 202 and sensing circuit 204 for delivery of stimulation and sensing of impedance or other signals. For example, the conductors may be used for impedance measurement when stimulation is not delivered, and vice versa.

FIG. 5 also shows reference electrode 408. Reference electrode 408 may be coupled to a reference (i.e., ground) node of stimulation sources 202 and provide a return path for stimulation current delivered via electrodes 116 of lead 114. Also, sensing circuit 204 may be coupled to reference electrode 408 to measure impedance between electrodes 116 and the reference electrode. As discussed above, reference electrode 408 may be provided in a variety of ways. For example, reference electrode 408 may be formed by selectively coupling one or more of electrodes 116 on lead 114 to the reference node of stimulation sources 202 via switch device 206A, 206B. In another example, reference electrode 408 may be carried by lead 114, e.g., as a dedicated reference electrode on lead 114. In additional examples, reference electrode 408 may be carried by IPG 106A, 106B, carried by a component coupled between the lead and IPG, such as lead coupling device 118, or provided elsewhere in IMD 100A, 100B.

Reference numeral 114 represents a lead (as shown in FIG. 1 and FIG. 3A) that includes electrodes 116 and associated conductors extending from contacts at a proximal end of the lead 114 to the electrodes 116. Reference numeral 110A represents a lead extension (as shown in FIG. 1 and FIG. 3A) coupled between lead 114 and an output of switch device 206A, e.g., via a connector 108A of IPG 106A. In this example, with lead extension 110A, switch device 206A is housed without IPG 106A as shown in FIG. 3A. In another example, reference numeral 110B represents a lead extension (as shown in FIG. 1 and FIG. 3B) coupled between sources 202, processor 210 and an input side of switch device 206B, e.g., via connector 108A of IPG 106B. In this example, with lead extension 110B, switch device 206B is housed in lead coupling device 118 or another device, external to IPG 106B, as shown in FIG. 3B.

Hence, in different examples, switch device 206A may be housed within IPG 106A or switch device 206B may be housed outside of IPG 106B. When housed outside of IPG 106B, switch device 206B may be housed within a lead coupling device 118 or other device, which may be configured to be mounted in a burr hole, mounted outside of the burr hole on the skull, carried by a portion of the lead body located within the cranium (e.g., a flex circuit carried by the lead), or carried by the body of lead extension 110A to couple output terminals of switch device 206B to conductors of lead 114. When switch device 206A is housed within IPG 106, conductors coupling electrodes 116 to the output of switch device 206A may run along the length of lead extension 110 and lead 114. For example, if there are N (e.g., N=40) electrodes, there may be N proximal contacts on lead extension 110A, coupled to N respective output terminals of switch device 206, N conductors running along lead extension 110, N distal contacts on lead extension 110A, N proximal contacts on lead 114, and N conductors running along lead 114 to independently deliver stimulation current to the individual electrodes. If there are M stimulation sources 202, switch device 206A may be controlled by processor 210 to couple one or more of the respective stimulation sources to respective electrodes via output terminals of the switch device 206A and the conductors and electrical contacts of lead extension 110 and lead 114. IPG 106A or 106B may include two or more stimulation sources, such that M is greater than or equal to two.

Lead extension 110 may extend over a distance of several centimeters between lead 114 and IPG 106, which may be implanted remotely from lead 114, e.g., under a clavicle of patient 112. When the number N of electrodes 116 is relatively high, it may not be desirable to have N separate conductors running along lead extension 110 from IPG 106 to lead 114. Alternatively, switch device 206B may be provided outside of IPG 106B, e.g., within an active lead coupling device 118B or other device, so that the N contacts and conductors extend only between the relatively nearby lead coupling device 118B and electrodes 116, rather than between the more remote IPG 106B and electrodes 116. In this case, stimulation sources 202, processor 210 and any other necessary components may be coupled to switch device 206B via lead extension 110B positioned between IPG 106B and active lead coupling device 118.

Instead of carrying N conductors, lead extension 110B, which may extend several centimeters between IPG 106B and lead coupling device 118, may include M conductors for M (e.g., M<N) respective stimulation sources 202, plus one or more conductors to carry control signals, timing signals, and/or other signals to switch device 206B from processor 210, and plus any suitable power and ground terminals for powering switch device 206B. Accordingly, in some examples, rather than carrying 40 conductors for 40 electrodes, lead extension 110B may carry conductors to couple two stimulation sources 202A, 202B to switch device 206B, with one or more additional conductors to couple processor 210, clock signals, power and ground to switch device 206B so that switch device 206B may be powered and controlled by processor 210. Sensing circuit 204 may be coupled to switch device 206B via one or more conductors or share one or more of the conductors that couple stimulation sources 202 to switch device 206B. In further examples, control signals generated by processor 210 may be carried together with other signals, such as power and/or clock signals, on the same conductor or conductors.

In either case, implantable electrodes 116 are coupled to IPG 106A or 106B via one or more implantable leads 114 and/or lead extensions 110A, 110B. Also, whether switch device 206A is housed within IPG 106A or switch device 206B is housed outside of IPG 106B within lead coupling device 118, processor 210 may control the switch device to selectively couple respective stimulation sources 202 to deliver electrical stimulation via individual electrodes, or allocate delivery of electrical stimulation to clusters of electrodes 116, e.g., based on impedance values of the electrodes. Again, processor 210 also may control switch device 206A or 206B to couple sensing circuit 204 to respective electrodes 116 to measure impedance values of the electrodes.

As shown in FIG. 5, processor 210 may select a group 402 of electrodes 116 of IMD 100A or 100B, as applicable, for delivery of electrical stimulation to the patient 112. Again, some operations of processor 210 may be performed by processor 302. For example, group 402 may be defined by processor 210, or defined by processor 302 of external programmer 104 and selected by processor 210 based on information transmitted to IMD 100A, 100B by the programmer. Group 402 of implantable electrodes 116, in various examples, may comprise all of the electrodes carried by implantable lead 114 or less than all of the electrodes carried by the lead. To reduce variation of current distribution among electrodes 116 in group 402, due to variations in impedance, processor 210 may perform impedance-based allocation of stimulation to clusters of electrodes within the group of electrodes.

For example, using the impedance values for electrodes 116, processor 210 may cluster group 402 of electrodes 116 into multiple clusters, e.g., two or more clusters. In the example of FIG. 5, processor 210 clusters electrodes 116 in group 402 into first cluster 404 of electrodes and second cluster 406 of electrodes. In particular, processor 210 may select a first cluster 404 of electrodes 116 in group 402 of electrodes based on impedance values of the electrodes in the first cluster. First cluster 404 of electrodes 116 may comprise less than all of the electrodes in the group 402 of the electrodes. Processor 210 may select a second cluster 406 of electrodes 116 in the group 402 of the electrodes based on impedance values of the electrodes in the second cluster. Again, in other examples, clusters may be selected by processor 210 based on information transmitted to IMD 100A, 100B by external programmer 104, e.g., in a case where processor 302 performs impedance-based clustering to select the clusters. Second cluster 406 of electrodes 116 is different than the first cluster 404 of the electrodes. Like first cluster 404, second cluster 406 of electrodes 116 may comprise less than all of the electrodes in group 402 of the electrodes. In general, clusters 404, 406 may be considered sub-groups of group 402, in that each cluster includes less than all of the electrodes in group 402.

Each of electrode clusters 404, 406 may include one, two or more of the plurality of the electrodes 116 of group 402. In some examples, each of clusters 404, 406 includes a plurality of electrodes 116 of group 402. In other examples, one of clusters 404, 406 may include a single electrode of electrodes 116 or group 402, while another of clusters 404, 406 includes a plurality of electrodes 116 of group 402. In further examples, the clustering algorithm may be configured so that processor 210 excludes generation of clusters with single electrodes, such that each cluster comprises a plurality of electrodes and no clusters have only a single electrode. Generation of clusters with single electrodes could be excluded, in some examples, for larger sets of electrodes, and permitted for smaller sets of electrodes. Again, although two clusters 404, 406 are shown in the example of FIG. 5, processor 210 (and/or processor 302), may generate more than two clusters, such as three, four or more clusters.

Processor 210 may control switch device 206A or 206B to couple first electrical stimulation source 202A to electrodes 116 in first cluster 404 of group 402, and couple second electrical stimulation source 202B to electrodes in second cluster 406 of the group. For example, first stimulation source 202A may be coupled to each of electrodes 116 in first cluster 404 such that the electrodes are connected in parallel to stimulation source 202A. Likewise, first stimulation source 202B may be coupled to each of electrodes 116 in second cluster 406 such that the electrodes are connected in parallel to stimulation source 202B. In each case, reference electrode 408 may provide a return path for stimulation delivered via electrodes 116 in first and second clusters 404, 406. Processor 210 controls switch device 206A or 206B and stimulation sources 202A and 202B to deliver a first portion of the electrical stimulation from first electrical stimulation source 202A of the IMD 100A or 100B via the first cluster 404 of implantable electrodes 116 in group 402 of the electrodes, and deliver a second portion of the electrical stimulation from second electrical stimulation source 202B of the IMD 100A or 100B via the second cluster 406 of the electrodes in the group of the electrodes. In this manner, processor 210 controls first stimulation source 202A to deliver a first portion of the electrical stimulation via the first cluster 404 of one or more electrodes 116 selected based on impedance values of the electrodes in the first cluster, and controls second stimulation source 202B to deliver a second portion of the electrical stimulation via a second cluster 406 of one or more electrodes selected based on impedance values of the electrodes in the second cluster.

IMD 100A or 100B may include two or more stimulation sources 202A-202M and, in some examples, may include only two stimulation sources 202A, 202B. In the example of FIG. 5, processor 210 controls stimulation sources 202A, 202B to deliver the first and second portions of the stimulation to clusters 404, 406, respectively, and controls the amplitudes of the first and second portions of the stimulation delivered by the stimulation sources. The amplitudes of the stimulation and the amplitudes of the first and second portions of the stimulation may be selected, for example, by processor 210 and/or by processor 302 of programmer 104. In the example in which more than two stimulation sources are available, more than two electrode clusters may be used to deliver stimulation at a given time, with each electrode cluster being coupled via switch device 206A or 206B to a respective one of the stimulation sources 202A-202M.

In the example of FIG. 5, group 402 comprises less than all of the plurality of implantable electrodes 116 of lead 114, first cluster 404 comprises less than all of the electrodes on lead 114 and less than all of the electrodes in group 402, and second cluster 406 comprises less than all of the electrodes in group 402 and less than all of the electrodes on lead 114. Electrodes in first cluster 404 are different than the electrodes in second cluster 406. Hence, cluster 404 may have a plurality of electrodes that are different from a plurality of electrodes in cluster 406. In this example, there is no overlap between one or more electrodes 116 in cluster 404 and the one or more electrodes in cluster 406 such that the electrodes in the electrode clusters are mutually exclusive.

The number of electrodes 116 in each of the clusters 404, 406 may be the same or different. In the example of FIG. 5, the number of electrodes in cluster 404 is different than the number of electrodes in cluster 406. The sum of the number of electrodes 116 in first cluster 404 and the sum of the electrodes in second cluster 406 may be equal to the number of electrodes in group 402. In this manner, stimulation sources 202A, 202B deliver stimulation via all of the electrodes 116 in group 402, but in separate portions allocated to first cluster 404 and second cluster 406, i.e., one portion of the stimulation delivered to cluster 404 by stimulation source 202A and another portion of the stimulation delivered to cluster 406 by stimulation source 202B.

In the example of FIG. 5, lead 114 carries 40 electrodes 116. In other examples, lead 114 may include less than 40 electrodes or greater than 40 electrodes. For example, the number of electrodes on lead 114 may be greater than or equal to 8 electrodes, greater than or equal to 16 electrodes, greater than or equal to 32 electrodes, or greater than or equal to 40 electrodes. With reference to the diagram of lead 114 in FIG. 1, FIG. 5 shows electrodes 116 arranged from most distal (1M, 1P, 1L, 1M) to most proximal (10M, 10P, 10L, 10A). Of the 40 electrodes 116 of lead 114, group 402 includes 16 electrodes that are selected for delivery of stimulation. In some examples, electrodes 116 in group 402 may be selected such that all electrodes are positioned together on lead 114, e.g., as shown in FIG. 5, where in this example group 402 includes electrodes grouped together at axial ring positions 1, 2, 3, 4 of lead 114. Alternatively, group 402 may be made up of electrodes 116 in two or more clusters that are not positioned together at the same axial or circumferential positions on lead 114. As an example, group 402 could include electrodes at ring levels 2, 3, 5 and 6, but not electrodes at ring level 4, or electrodes at circumferential positions M and P but not L and A.

In the example of FIG. 5, first cluster 404 includes 4 of the 16 electrodes of group 402, and second cluster 406 includes 12 of the 16 electrodes of group 402. Electrodes 116 in each cluster 404, 406 form part of group 402 and may be positioned adjacent one another on lead 114. Alternatively, a given cluster 404, 406 may include some electrodes that are within group 402 but are not immediately adjacent to one another, either axially in adjacent ring levels or circumferentially within a given axial ring position. In the example of FIG. 5, cluster 404 includes electrodes 1M, 1P, 1L and 1A, while cluster 406 includes electrodes 2M, 2P, 2L, 2A, 3M, 3P, 3L, 3A, 4M, 4P, 4L and 4A. The electrodes 116 may be clustered in first and second clusters 404, 406 based on similarity of measured impedance values of the electrodes, permitting impedance-based allocation of portions of the stimulation generated by stimulation sources 202 to the clusters, e.g., to reduce variation in current output distribution among the electrodes in group 402 and promote generation of a more uniform stimulation field.

Selection of the electrodes 116 in the first and second clusters 404, 406, in some examples, may include selecting the first and second clusters based on k-means clustering of the electrodes in group 402 of electrodes. For example, upon selecting a group 402 of electrodes 116, and based on measured impedance values obtained by sensing circuit 204 for electrodes in the group, processor 210 (or possibly processor 302 of external programmer 104 or another device) may perform a k-means clustering algorithm to assign electrodes to clusters having the nearest mean impedance values relative to the impedance values of the respective electrodes. In some examples, upon performing a clustering algorithm, such as a k-means clustering algorithm, processor 302 may assign electrodes 116 to clusters, such that the electrodes in first cluster 404 have a mean impedance value that is less than a mean impedance value of the electrodes in second cluster 406.

Stimulation source 202A and stimulation source 202B may deliver the first and second portions of the electrical stimulation to clusters 404, 406, respectively, simultaneously or substantially simultaneously. In other cases, stimulation sources 202A, 202B may deliver the first and second portions of the electrical stimulation to clusters with a time offset between these portions. Processor 210 may select amplitudes of the first and second portions such that a sum of the first and second portions is equal to a desired total amplitude of the stimulation to be delivered via electrodes 116 in group 402, such as a current amplitude in the case of a regulated current provided by the stimulation sources. In addition, processor 210 may select the first and second portions of the electrical stimulation delivered by stimulation source 202A and stimulation source 202B, respectively, such that an average per-electrode amplitude of the electrical stimulation delivered to electrodes 116 in first cluster 404 is substantially the same as an average per-electrode amplitude of the electrical stimulation delivered to the electrodes in second cluster 406, where the average is an arithmetic mean.

In an example in which a number of electrodes 116 in first cluster 404 is different than a number of the electrodes in second cluster 406, e.g., as shown in FIG. 5, an amplitude of the first portion of the electrical stimulation delivered to the electrodes in the first cluster is different than the amplitude of the second portion of the electrical stimulation delivered to the electrodes in the second cluster. For example, if the desired total stimulation amplitude is 2.0 milliamps for a group 402 of 16 electrodes, first cluster 404 has 4 electrodes, and second cluster 406 has 12 electrodes, then, to maintain the same average per-electrode amplitude of the electrical stimulation delivered via the first and second clusters, the first portion delivered via the first cluster of 4 electrodes would be 0.5 milliamps (0.125 milliamps per electrode) and the second portion delivered via the second cluster of 12 electrodes would be 1.5 milliamps (0.125 milliamps per electrode). Hence, each of the two or more clusters formed by the impedance-based allocation technique may have a plurality of electrodes of the group 402 of electrodes. For example, a first cluster 404 may comprise a first plurality of the electrodes in the group of the electrodes and a second cluster 406 may comprise a second plurality of the electrodes in the group of electrodes. In other examples, one of the clusters produced by the impedance-based allocation process may comprise a single electrode of the group of the electrodes, and one or more other clusters may have a plurality of electrodes of the group of the electrodes. In further examples, generation of clusters with single electrodes could be prohibited in the impedance-based allocation process, such that all clusters have multiple electrodes. These portions of the stimulation delivered to the clusters sum to the total desired stimulation amplitude of 2.0 milliamps for the entire group 402 of electrodes. The group 402 of electrodes 116 may be specified, for example, manually by a clinician or automatically by a program executed by IMD 100 or external programmer 104. Likewise, a desired total stimulation to be delivered by group 402 of electrodes 116 may be specified automatically or manually, e.g., by a clinician. As one example, a clinician may select a group 402 of electrodes 116 and specify a desired total amplitude of electrical stimulation to be delivered via the group of electrodes, e.g., by user input received by external programmer 104.

In some examples, to select the first cluster 404 and second cluster 406 of electrodes 116 based on impedance values of the electrodes, processor 210 may select the first cluster of the electrodes based on output current values determined for each of the electrodes in the first cluster as a function of the impedance values of the respective electrodes in the first cluster, and select the second cluster of the electrodes based on output current values determined for each of the electrodes in the second cluster as a function of the impedance values of the respective electrodes in the second cluster. For example, processor 210 may simulate the distribution of electrical current among the electrodes 116 on the assumption that stimulation current is delivered by a single stimulation source to all electrodes in group 402, e.g., at a total current level desired for the group, then partition the resulting current distribution values (rather than the impedance values themselves) for the respective electrodes with the k-means clustering algorithm, and bin each of the electrodes into one of the two clusters 404, 406 with the mean current value nearest the current value of the respective electrode. In an example, the simulated current distribution for each electrode may be determined, e.g., by processor 210, based on the overall current to be delivered in parallel to the electrodes in the group 402, the impedance of the group of electrodes, and the impedance value of the respective electrode, e.g., as $I_X = I * R_T/R_X$ milliamps, where $I_X$ is the current distribution value of the electrode, $R_X$ is the impedance value of the electrode, I is the total current for all electrodes in the group, and $R_T$ is the total impedance for all of the electrodes in the group.

Again, the number of clusters may be defined by the number of available amplitude sources, which in this example of FIG. 5 is two sources 202A and 202B. Additionally, or alternatively, the number of clusters may be defined by a power consumption threshold in relation to power consumption produced by stimulation sources 202. Power consumption may increase as additional stimulation sources are added, e.g., due to increased overhead associated with current or voltage regulation, increased switching, or other power consumption activity. In this case, a processor, e.g., processor 210 (and/or processor 302), may limit the number of clusters generated by a clustering algorithm, such a k-means clustering algorithm, to correspond to a number of stimulation sources 202 sufficient to maintain power consumption at a level below a desired power consumption threshold. For example, if power consumption associated with M stimulation sources is below the desired power consumption threshold, but power consumption associated with M+1 stimulation sources is above the desired power consumption threshold, processor 210 may limit the number of clusters produced by the clustering algorithm to be M or less, thereby keeping the number of stimulation sources at M or less, and keeping power consumption below the threshold.

Whether the k-means clustering algorithm clusters electrodes based on impedance values of the electrodes, or as a function of current distribution values determined based on a desired total stimulation amplitude and the impedance values, processor 210 bins the electrodes into clusters based on impedance values of the electrodes, either directly or indirectly. In one example, processor 210 may initially set the number of clusters according to the number of stimulation sources 202 available for delivery of stimulation in the IPG 106A, 106B. If there are two available stimulation sources 202A, 202B, processor 210 may set the number of clusters to 2. Given the initial set of electrodes in group 402, and either measured impedance values for the electrodes or current distribution values for each electrode determined based on a desired stimulation amplitude and the measured impedance values, processor 210 may perform the k-means clustering algorithm to generate clusters associated with different mean values (e.g., of impedance or current) of the electrodes in the group, e.g., two clusters with two respective mean values in the case of two available stimulation sources.

Processor 210 may initially establish the electrode clusters by selecting values from the set of values (impedance or current) for the electrodes as the initial means for the clusters, using any of a variety of initialization techniques. For example, the initial means values could be selected randomly. Upon establishing the initial clusters, processor 210 assigns electrodes to the clusters. For example, each electrode may be assigned to a cluster having a mean value (impedance or current) that is nearest to the value (impedance or current) of the respective electrode. In some examples, the k-means clustering algorithm may be seen as assigning electrodes to the nearest cluster based on a distance between the values of each electrode and the mean value of the cluster. Again, although impedance-based allocation operations may be performed by processor 210, some of such operations could be performed by processor 302 or by processor 210 in combination with processor 302.

Upon assigning the electrodes to the clusters, processor 210 may perform one or more iterations in which the means of the clusters are updated based on the values of the electrodes in the clusters, and electrodes are reassigned to the clusters. For example, at each iteration, the centroid of a cluster, resulting from assignment of one or more electrodes to that cluster, may become the new mean for that cluster for the next assignment iteration, which may result in reassignment of some electrodes between clusters. As electrodes are assigned and reassigned to clusters based on nearest distance, some clusters may have more electrodes than other clusters. For example, FIGS. 6A, 6B, 8, 10 show a case in which four electrodes are assigned to a first cluster and twelve electrodes are assigned to a second cluster. The iterative process may terminate after a predetermined number of iterations, i.e., 2, 3 or more iterations, or until the algorithm converges to a point that reassignments of electrodes among clusters no longer change. It is also possible that the algorithm could terminate in a single step after the initial assignment of electrodes to clusters, e.g., if the initial means for the clusters were selected in a reliable way.

Although k-means clustering is described for purposes of example, processor 210 (and/or processor 302) may be configured to use other algorithms to cluster electrodes 116. For example, processor 210 (and/or processor 302) could use other algorithms such as distribution-based clustering, density-based clustering or hierarchical clustering algorithms to generate clusters of electrodes based on impedance values of the electrodes, e.g., based directly on the impedance values or based on simulated current distribution values that are determined based on the impedance values, e.g., determined based on impedance values and stimulation amplitudes, such as electrical current amplitudes, that would be delivered to the group of electrodes.

As a further example, processor 210 (and/or processor 302) could be configured to use a sorting algorithm as a clustering algorithm to generate clusters of electrodes. Using a sorting algorithm, processor 210 (and/or processor 302) may sort electrodes into clusters based on impedance values, either directly or based on current distribution values that are determined based on impedance values. In this manner, processor 210 (and/or processor 302) may sort electrodes from highest impedance to lowest impedance, or lowest current value to highest current value, and assign the electrodes to clusters based on rank. For example, a group of electrodes with lowest current values (or highest impedance values) may be placed in a first cluster, a group of electrodes with next lowest current values (or next highest impedance values) may be placed in a second cluster, and so forth. The clusters generated by the sorting algorithm may have the same number of electrodes, i.e., same size, or different numbers of electrodes. The sizes of clusters may be predetermined by processor 210 (and/or processor 302), e.g., based on the number of active electrodes and/or number of available stimulation sources. In some examples, a smaller size could be set for a cluster of higher impedance (or lower current) electrodes relative to a larger size for one or more clusters of lower impedance (or higher current) electrodes.

Impedance measurements may be measured initially upon implantation of IMD 100A, 100B, or prior to activation of the IMD, and used either directly or by way of current values determined based on a desired stimulation amplitude and the impedance values, in impedance-based allocation techniques described in this disclosure. For example, sensing circuit 204 may measure impedance values for all electrodes carried by lead 114, and then processor 210 may use the impedance values in the clustering algorithm (or transmit information indicating the impedance values to programmer 104 for use by processor 302 in the clustering algorithm). For example, processor 210 (and/or processor 302) may use the impedance values in the clustering algorithm when a new therapy program is activated or therapy parameters of a therapy program are modified. Hence, the clustering algorithm and impedance-based allocation may be repeated when therapy changes, using the initially measured impedance values. Additionally, or alternatively, in some examples, the clustering algorithm and impedance-based allocation may be repeated with newly updated, impedance values for the electrodes. For example, some or all of the impedance values may be re-measured each time a new therapy program is activated or therapy parameters are adjusted, or each time the clustering algorithm and impedance-based allocation is performed.

As a further alternative, in some examples, the impedance values may be re-measured by sensing circuit 204 for use in the clustering algorithm and impedance-based allocation at various times, such as, e.g., during clinic visits to a clinician by a patient, upon remote interrogation and programming by a clinician, at regular or scheduled intervals, and/or in response to sensed events or conditions, such as changes in physiological signals or brain signals. In this manner, impedance values may be re-measured at various times to account for changes in impedance, permitting re-clustering (i.e., modified clustering) of electrodes, re-allocation of stimulation sources to electrodes clusters, and/or re-allocation of stimulation amplitudes to electrode clusters based on impedance changes.

Processing associated with impedance-based allocation may be performed by processor 210 in IPG 106A, 106B. As mentioned above, alternatively, some of the processing could be provided in whole or in part by other processors, such as processor 302 of external programmer 104. For example, in another implementation, electrode impedance values measured by sensing circuitry 204 may be transmitted by processor 210 to external programmer 104 via telemetry interface 208, 308. In this case, processor 302 may select the first and second clusters of electrodes, e.g., using a k-means clustering algorithm or another algorithm, and transmit instructions or other information to processor 210 via telemetry interface 208, 308 indicating the electrodes selected for the clusters and/or specifying the amplitudes of first and second portions of the electrical stimulation to be delivered to the respective clusters by stimulation sources 202A, 202B. Processor 302 may also transmit to processor 210, in some examples, information indicating the electrodes selected for the group of electrodes 116 and the overall amplitude of the electrical stimulation to be delivered by the group.

Accordingly, in this example, IPG 106A, 106B may measure the electrode impedance values of electrodes in group 402, transmit information representative of the measured impedance values of the electrodes to external programmer 104, and select the first cluster 404 of the electrodes, the second cluster 406 of the electrodes, an amplitude of the first portion of the electrical stimulation delivered by stimulation source 202A to the first cluster, and an amplitude of the second portion of the electrical stimulation delivered by stimulation source 202B to the second cluster, based on instructions or information received from the external programmer 104. Hence, processing may be performed by processor 210 and/or processor 302, e.g., for selection of electrodes in the clusters and/or definition of amplitudes of portions of the stimulation delivered by stimulation sources to the clusters. In either case, processor 210 controls one or more switch devices 206A, 206B to couple each of the electrodes 116 of the first cluster 404 of electrodes to the first electrical stimulation source 202A to deliver the first portion of the electrical stimulation, and couple each of the electrodes of the second cluster 406 of electrodes to the second electrical stimulation source 202B to deliver the second portion of the electrical stimulation.

Figures 6A, 6B:
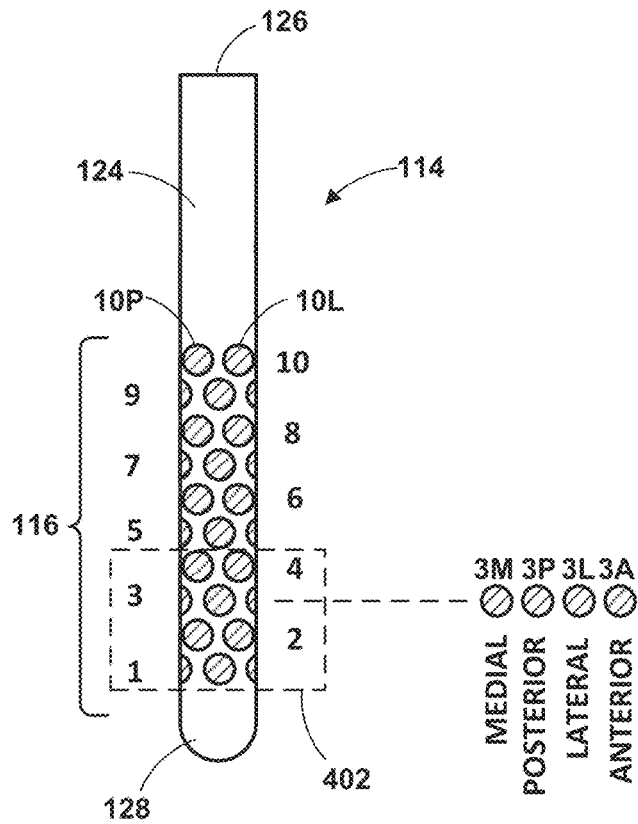
FIG. 6A is a schematic diagram illustrating a group of active electrodes on the implantable DBS lead of FIG. 2.
FIG. 6B is a table illustrating an example of measured impedance values for the group of active electrodes shown in FIG. 6A.

FIG. 6A is a schematic diagram illustrating a group 402 of active electrodes 116 on the implantable DBS lead 114 of FIG. 2. Group 402 of electrodes 116 is shown on a single lead 114 in FIG. 6A. Alternatively, group 402 of electrodes 116 could be provided on multiple leads. In the example of FIG. 6A, group 402 includes 16 electrodes 116 at axial positions 1, 2, 3 and 4 of lead 114. Accordingly, 16 of the 40 electrodes carried by lead 114 are selected for delivery of stimulation. In this example, two stimulation sources 202A, 202B are assumed to be available in IPG 106A, 106B, and total stimulation output current amplitude via electrodes 116 in group 402 is selected to be 2.0 mA.

FIG. 6B is a table illustrating an example of measured impedance values for group 402 of active electrodes 116 shown in FIG. 6A. As shown in FIG. 6B, heterogeneous tissue conductivity results in an impedance range of (5068, 9953) ohms between each electrode 116 in group 402 and a reference electrode on IPG 106A, 106B. Impedance may be measured between electrodes 116 on lead 114 and a reference electrode (e.g., reference electrode 408 shown in FIG. 5), which may be formed by any of a variety of components of IMD 100A, 100B, such as a dedicated reference electrode carried by IPG 106A, 106B, e.g., on a case of the IPG, a dedicated reference electrode formed on lead 114 or on lead coupling device 118 between lead 114 and IPG 106A, 106B, a reference electrode provided by selective switching by switch device 206A, 206B to couple of one or more of the electrodes 116 to a ground node of stimulation sources 202 to serve as a reference electrode, or a reference electrode provided elsewhere within IMD 100A, 100B. In each case, the respective reference electrode may be coupled to a ground node of stimulation sources 202 to provide a return path for stimulation delivered by active electrodes 116, and sensing circuit 204 may measure impedance of each electrode based on impedance between the respective electrode and the reference electrode.

In the example of FIG. 6B, the reference electrode is provided on a case of IPG 106A, 106B. Accordingly, impedance is measured between each electrode 116 and the reference electrode formed on the case of IPG 106A, 106B. In addition, a reference node of stimulation sources 102 is coupled to a reference electrode provided on the case of IPG 106A, 106B, e.g., to provide a return path for stimulation current. The table of FIG. 6B shows that medial, posterior, lateral and anterior electrodes in axial ring 1 have measured impedance values of 5068, 5406, 5774 and 6081 ohms, respectively. Medial, posterior, lateral and anterior electrodes in axial ring 2 have measured impedance values of 6314, 6647, 6979 and 7312 ohms, respectively, medial, posterior, lateral and anterior electrodes in axial ring 3 have measured impedance values of 7634, 7966, 8298 and 8630 ohms, respectively, and medial, posterior, lateral and anterior electrodes in axial ring 4 have measured impedance values of 8957, 9289, 9621 and 9953 ohms, respectively.

Figure 9:
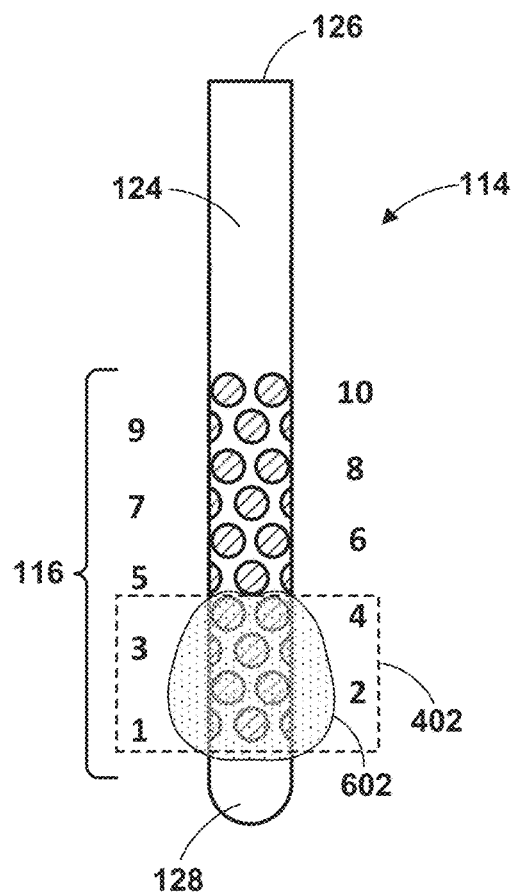
FIG. 9 is a conceptual diagram illustrating stimulation field distribution for the group of active electrodes of FIG. 6A when impedance-based allocation of stimulation sources is not used and the electrodes are driven by one stimulation source.

FIG. 7 is a table illustrating an example of current distribution values for the group 402 of active electrodes shown in FIG. 6A when impedance-based allocation of stimulation sources 202 is not used and the electrodes 116 in group 402 are driven by one stimulation source. FIG. 9 is a conceptual diagram illustrating stimulation field distribution for the group 402 of active electrodes of FIG. 6A when impedance-based allocation of stimulation sources is not used and the electrodes are driven by one stimulation source 202.

Figure 10:
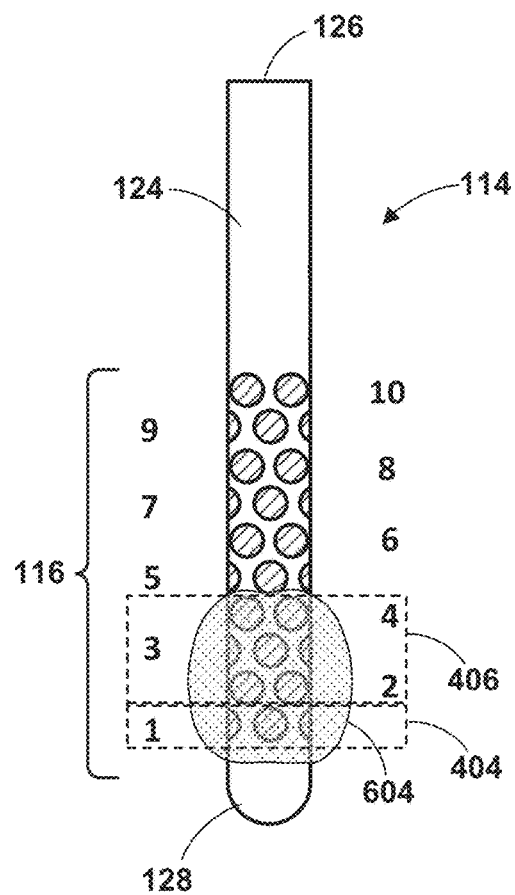
FIG. 10 is a conceptual diagram illustrating stimulation field distribution for a group of active electrodes of FIG. 6A when impedance-based allocation of stimulation sources is used and clusters of the electrodes are driven with different stimulation sources.

FIG. 8 is a table illustrating an example of current distribution values for the group 402 of active electrodes 116 shown in FIG. 6A when impedance-based allocation of stimulation sources is used and clusters 404, 406 of the electrodes are driven with different stimulation sources 202A, 202B, respectively. FIG. 10 is a conceptual diagram illustrating stimulation field distribution for a group 402 of active electrodes of FIG. 6A when impedance-based allocation of stimulation sources is used and clusters 404, 406 of the electrodes are driven with different stimulation sources 202A, 202B.

Without impedance-based allocation of stimulation amplitude sources (and instead utilizing only one stimulation source for all electrodes in group 402), the distribution of current output is rather heterogeneous with a range (0.09, 0.24), as shown in FIG. 7. In particular, the table of FIG. 7 shows that, without impedance-based allocation, medial, posterior, lateral and anterior electrodes in axial ring 1 have current distribution values of 0.24, 0.22, 0.20, and 0.18 milliamps, respectively. Without impedance-based allocation, medial, posterior, lateral and anterior electrodes in axial ring 2 have current distribution values of 0.13, 0.11, 0.10 and 0.09 milliamps, respectively, medial, posterior, lateral and anterior electrodes in axial ring 3 have measured impedance values of 0.09, 0.09, 0.08, and 0.08 milliamps, respectively, and medial, posterior, lateral and anterior electrodes in axial ring 4 have measured impedance values of 0.11, 0.10, 0.09, and 0.09 milliamps, respectively.

As shown in FIG. 9, a stimulation field 602 produced by group 402 of electrodes 116 of lead 114, without impedance-based allocation, tends to be significantly non-uniform. In particular, due to impedance variation among the electrodes in group 402, significantly more current is distributed from electrodes (with lower impedance values) at axial ring 1 compared to electrodes (with higher impedance values) at other axial rings, e.g., rings 2, 3 and 4, causing stimulation field 602 to have a non-uniform shape.

In the example of FIG. 9, without impedance-based allocation, the non-uniform shape of stimulation field 602 is shown by a field that extends further radially outward at areas near axial rings 1 and 2, and extends significantly less at axial rings 3 and 4, than at axial rings 1 and 2. Hence, when electrodes 116 with different impedance values are driven in common by one stimulation source 202, e.g., such that the electrodes are coupled in parallel with one another, the result may be varying current distribution among the electrodes and non-uniform distribution of stimulation field 602.

When impedance-based allocation of amplitude sources 202A, 202B is applied, the current heterogeneity is reduced with a range of (0.09, 0.18) as shown in the table of FIG. 8. By applying impedance-based allocation of stimulation amplitude sources, the current distribution range can be reduced and a more homogenous stimulation field may be delivered to the tissue, e.g., as shown in FIG. 10. In this example, the impedance-based allocation of stimulation amplitude sources resulted in two clusters with 4 electrodes in a first cluster 404 and 12 electrodes in a second cluster 406, with stimulation amplitudes of 0.5 and 1.5 milliamps (mA), respectively.

In this example, a clustering algorithm, such as a k-means clustering algorithm, performed by processor 210 results in assignment of the electrodes in axial ring 1 to cluster 404 and assignment of the electrodes in axial rings 2, 3, and 4 to cluster 406. In particular, the table of FIG. 8 shows that, with impedance-based allocation, electrodes 116 at medial, posterior, lateral and anterior positions in axial ring 1, assigned to first cluster 404, have current distribution values of 0.15, 0.13, 0.12 and 0.10 milliamps, respectively. Also, with impedance-based allocation, electrodes in second cluster 406 have current distribution values as follows: medial, posterior, lateral and anterior electrodes in axial ring 2 have current distribution values of 0.18, 0.16, 0.15 and 0.14 milliamps, respectively, medial, posterior, lateral and anterior electrodes in axial ring 3 have measured impedance values of 0.12, 0.11, 0.10, and 0.09 milliamps, respectively, and medial, posterior, lateral and anterior electrodes in axial ring 4 have measured impedance values of 0.13, 0.11, 0.11, and 0.10 milliamps, respectively.

As shown in FIG. 10, stimulation field 604 produced by impedance-based clusters 404 and 406 of electrodes 116, when impedance-based allocation is used, may be significantly more uniform than stimulation field 602 produced in the example of FIG. 9 when impedance-based allocation is not used. When impedance values (or simulated current distribution values determined as a function of impedance values) of electrodes 116 in group 402 are used to divide the electrodes into clusters 404, 406, and each cluster is driven by different stimulation sources 202A, 202B with separately controlled amplitudes, variation in current distribution among the electrodes may be reduced. In particular, by assigning electrodes to clusters based on similarity of impedance values (e.g., by assigning electrodes to clusters having mean impedance values or mean current values that are closest to the impedance values or current values of the electrodes), and then defining particular stimulation amplitudes (e.g., current amplitudes) for the respective clusters, e.g., based on the number of electrodes in the clusters, variation in the current output of the electrodes in group 402 may be reduced.

With a reduction of impedance variation among electrodes in each cluster 404, 406, and allocation of particular stimulation amplitudes to the electrodes in each cluster, more similar amounts of current may be distributed from electrodes 116 of group 402, causing stimulation field 604 to have a more uniform shape, as shown in FIG. 10. In the example of FIG. 10, with impedance-based allocation, the more uniform shape of stimulation field 604 is shown by a field that extends radially outward to a similar extent at an area near axial rings 1 and 4, and to a similar extent at an area near axial rings 2 and 3, even though actual impedance values for electrodes in axial ring 1 compared to electrodes in axial ring 4 are significantly different. Hence, when electrodes 116 with different impedance values are divided into clusters 404, 406, and electrodes in each of the clusters are driven in common with a selected current amplitude by one of two different stimulation sources 202A, 202B, e.g., such that the electrodes in a cluster are coupled in parallel with one another, the result may be less variation in current distribution among the electrodes and more uniform stimulation field distribution.

In the example of FIG. 10, group 402, and clusters 404 and 406, include all of the electrodes from each of a plurality of complete rings. In particular, in the example of FIG. 10, group 402 includes medial, posterior, lateral, and anterior electrodes for each of the rings at axial positions 1, 2, 3 and 4. In other examples, group 402 may include less than all electrodes for one or more rings. For example, group 402 could be defined to include only one or some, but not all, electrodes for a given ring at a particular axial position, e.g., only medial and posterior but not lateral and interior at a given ring. Accordingly, illustration of group 402 as including all electrodes for each of the rings at axial positions 1, 2, 3 and 4 in FIG. 10 is for purposes of example. Also, although each of clusters 404, 406 in the example FIG. 10 includes all electrodes for respective rings in the clusters, the impedance-based clustering algorithm may define clusters that include only one or some, but not all, electrodes for a given ring at a particular axial position, based on measured impedance values of the electrodes. For example, depending on impedance, clusters 404, 406 could each include different electrodes from the same ring. Hence, one or more electrode clusters may include less than all electrodes from an axial ring. For example, one electrode cluster may include some electrodes from a particular axial ring and another electrode cluster may include one or more remaining electrodes from that same axial ring. Whether or not all electrodes from an axial ring are included in the same cluster may be dependent on the respective electrode impedances.

Although the examples in FIGS. 8 and 10 make use of two clusters and two stimulation sources 202A, 202B, in other examples, more than two stimulation sources, such as three, four or more stimulation sources (e.g., stimulation sources 202A, 202B, and optionally additional stimulation sources through stimulation source 202M as shown in FIG. 5), and a corresponding number of more than two clusters, such as three, four or more clusters, may be used to deliver more than two different portions, such as three, four or more portions, of the stimulation to electrodes in the respective clusters.

In some examples, the k-means clustering algorithm, or a similar clustering algorithm, may be configured to generate a number of clusters that is equal to the number of stimulation sources 202 that are either selected for delivery of stimulation or available for delivery of stimulation. For example, if there are 4 stimulation sources available in an IPG 106A, 106B, a clustering algorithm configured to use all available stimulation sources may generate 4 clusters. Similarly, if there are 2 stimulation sources available in an IPG 106A, 106B, as in the example of FIGS. 8 and 10, a clustering algorithm configured to use all available stimulation sources may generate 2 clusters. Alternatively, if there are 4 stimulation sources available in an IPG 106A, 106B, but a therapy program or clinician specifies the use of only 2 stimulation sources (or directly specifies the use of 2 clusters), a clustering algorithm configured to use selected stimulation sources may then generate 2 clusters.

Figure 11:
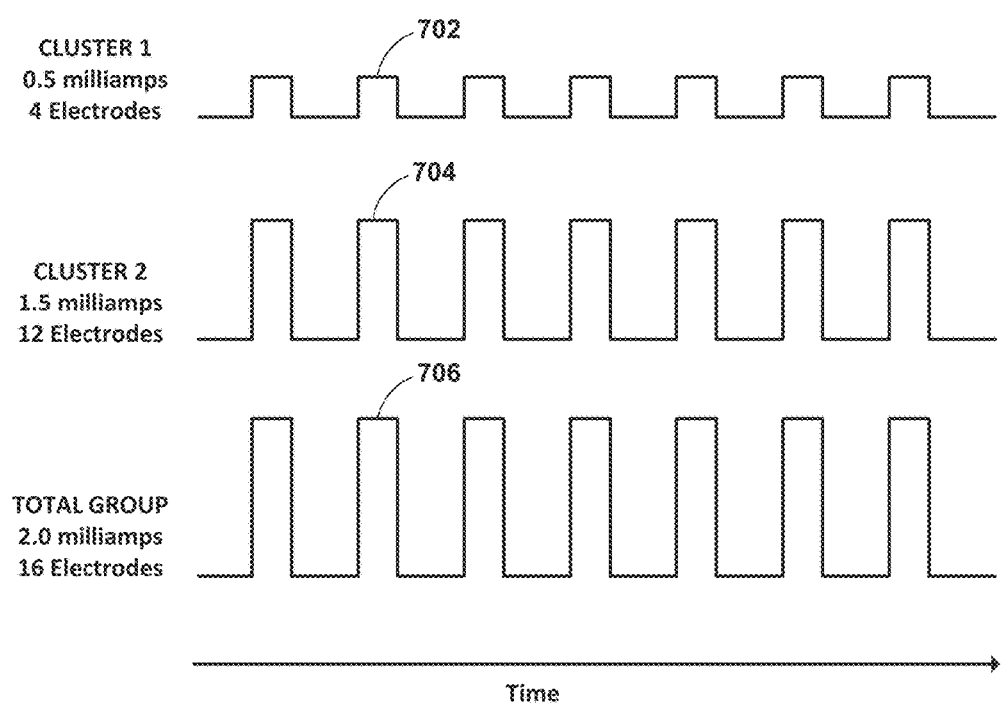
FIG. 11 is a timing diagram illustrating delivery of stimulation from multiple stimulation sources via multiple clusters of active electrodes using impedance-based allocation of stimulation sources.

FIG. 11 is a timing diagram illustrating delivery of stimulation over time from multiple stimulation sources (e.g., two stimulation sources 202A, 202B) via multiple clusters (e.g., 2 clusters 404, 406) of active electrodes 116 in a group 402 using impedance-based allocation of the stimulation sources. In the example of FIG. 11, stimulation sources 202A, 202B may be cathodic current sources that deliver, i.e., source, electrical stimulation current to electrodes 116. In this case, an anode on lead 114 or on a case of IPG 106A, 106B may provide a reference electrode, i.e., return or ground electrode, for the stimulation current. Alternatively, stimulation sources 202A, 202B may be anodic current sources that deliver, i.e., sink, electrical stimulation current from electrodes 116. In this case, a cathode on lead 114 or on a case of IPG 106A, 106B may source the stimulation current. In general, cathodic current sources 202A, 202B will be described in this disclosure for purposes of illustration. In either case, a reference electrode may provide a return electrode for stimulation and a reference electrode for impedance measurement, e.g., measurement by sensing circuit 204 of impedance between an electrode 116 and the reference electrode.

In other examples, electrodes 116 on leads 114 may include groups of one or more cathodes and groups of one or more anodes, in which case stimulation sources 202A, 202B may include current sources or current sinks, as applicable. In such a case, impedance-based allocation of stimulation may be applied to a group of cathodes and/or separately to a group of anodes to reduce variation in current output or input among the electrodes.

As shown in FIG. 11, for a therapy program that specifies delivery from a stimulation source of 2.0 milliamps of stimulation current amplitude across electrodes in group 402 in parallel, such that the 2.0 milliamps is divided across the multiple electrodes, processor 210 (or processor 302 of programmer 104 in other examples) performs a clustering algorithm as described in the disclosure, e.g., based on impedance values obtained for electrodes in group 402 by sensing circuit 204, and allocates portions of the stimulation amplitude to be delivered by respective stimulation sources 202A, 202B to resulting clusters 404, 406 of electrodes.

In the example of FIG. 11, the clustering algorithm results in a first cluster 404 of 4 electrodes and a second cluster 406 of 12 electrodes, e.g., as described with reference to FIGS. 5, 8 and 10. Processor 210 controls stimulation sources 202A to deliver a first portion 702, with a pulse amplitude at 0.5 milliamps, of the overall stimulation amplitude of 2.0 milliamps, via the 4 electrodes in first cluster 404, and controls stimulation source 202B to deliver a second portion 704, at a pulse amplitude of 1.5 milliamps, of the overall stimulation amplitude of 2.0 milliamps via the 12 electrodes of second cluster 406. Processor 210 sets the first and second portions of the stimulation amplitude so that the average per-electrode stimulation amplitude for electrodes across the entire group 402 is the same for electrodes in cluster 404 and electrodes in cluster 406. In particular, in this example, by setting the first portion to 0.5 milliamps and setting the second portion to 1.5 milliamps, a total of 2.0 milliamps of stimulation pulse current amplitude, shown by total stimulation 706, is delivered by stimulation source 202A and stimulation source 202B, and the per-electrode average current amplitude for all active electrodes (i.e., the electrodes in clusters 404 and 406 of group 402) is 0.125 milliamps.

Figure 12:
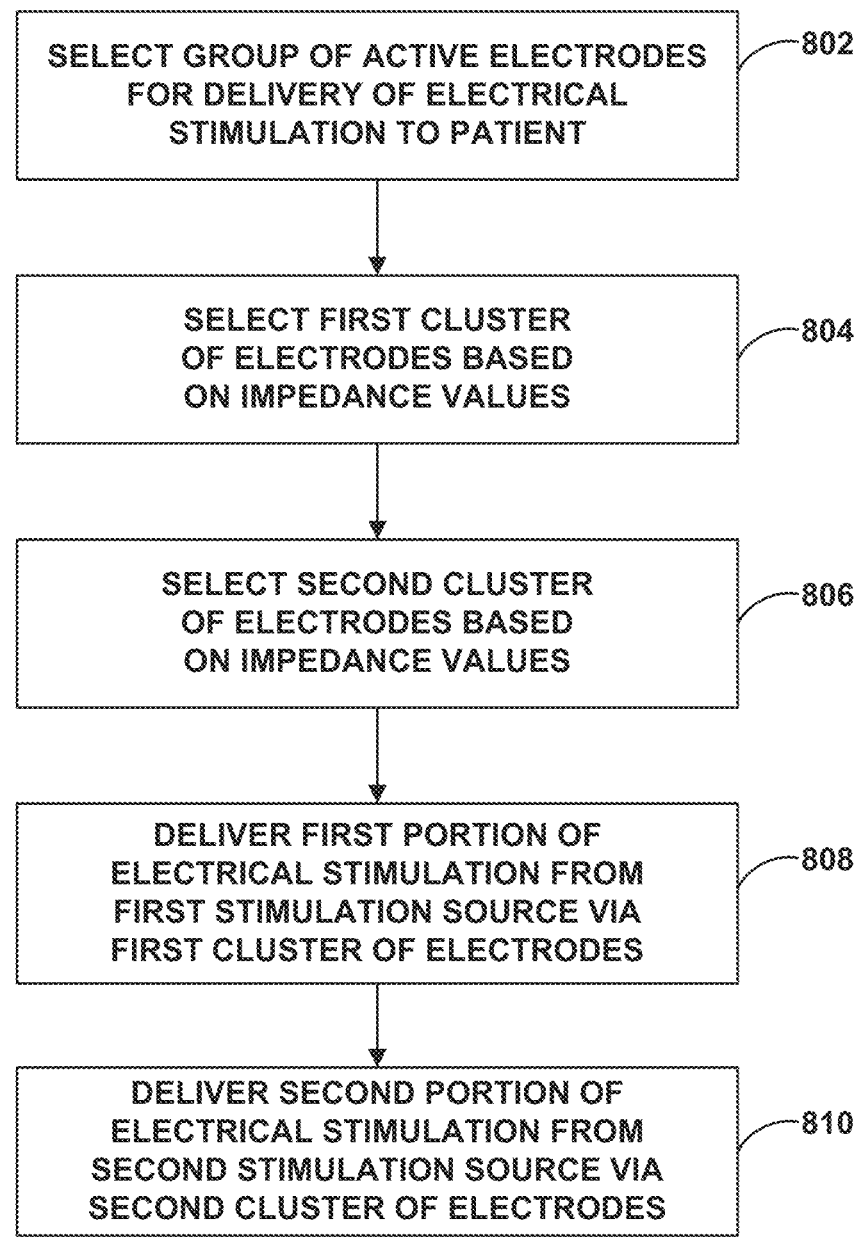
FIG. 12 is a flowchart illustrating an example of a method for delivering stimulation from multiple stimulation sources via multiple clusters of active electrodes using impedance-based allocation of stimulation sources.

As further shown in FIG. 11, under control of processor 210, stimulation source 202A delivers the first portion 702 of the stimulation (0.5 milliamps) to electrodes in the first cluster 404 (Cluster 1) simultaneously or substantially simultaneously with delivery of the second portion 704 of the stimulation (1.5 milliamps) to electrodes in the second cluster 406 (Cluster 2) by stimulation source 202B. For example, if overall stimulation has a pulse width and pulse rate, then each of the first and second portions of stimulation also have that pulse width and pulse rate, and are delivered in-phase with one another to realize, in combination, an overall delivery of stimulation to group 402 (Total Group) with a pulse amplitude of 2.0 milliamps. Hence, the first and second portions of the stimulation for the clusters may have the same pulse width and pulse rate, and be delivered simultaneously and in-phase with one another, but have different amplitudes that sum to the desired total amplitude (e.g., 2.0 milliamps in the example of FIG. 11) and are selected, e.g., as a function of the number of electrodes in each cluster, to yield the same or substantially the same per-electrode average current values FIG. 12 is a flowchart illustrating an example of a method for delivering stimulation from multiple stimulation sources 202 via multiple clusters of active electrodes 116 of an implantable lead 114 of an IMD 100A, 100B using impedance-based allocation of stimulation sources. The method may be performed by various components of IMD 100A, 100B, as described in this disclosure. For example, the method may be performed by processor 210 or by processor 210 in combination with other components of IMD 100A, 100B. In some examples, processor 210 or processor 302 of programmer 104 may perform various aspects of the method, such as selecting clusters of electrodes. In additional examples, various aspects of the method may be performed by a combination of processor 210 of IMD 100A, 100B and processor 302 of programmer 104.

As shown in FIG. 12, the method may comprise selecting, e.g., by processor 210, a group 402 of a plurality of implantable electrodes of the IMD for delivery of the electrical stimulation to the patient (802), selecting, e.g., by processor 210, a first cluster 404 of one or more of the electrodes in the group of electrodes based on impedance values of the electrodes in the first cluster (804), the first cluster of one or more electrodes comprising less than all of the electrodes in the group of the plurality of implantable electrodes, and selecting, e.g., by processor 210, a second cluster 406 of one or more of the electrodes in the group of the plurality of implantable electrodes based on impedance values of the electrodes in the second cluster (806), the second cluster of one or more electrodes being different than the first cluster of one or more electrodes and comprising less than all of the electrodes in the group of the plurality of implantable electrodes.

Although two clusters 404, 406 are described in the example of FIG. 12, processor 210 (or processor 302), may generate more than two clusters, such as three, four or more clusters of the electrodes 116 of group 402. Each of the two or more electrode clusters may include a plurality of the electrodes 116 of group 402. For example, first cluster 404 may comprise a first plurality of the electrodes in group 402 of electrodes 116 and second cluster 406 may comprise a second plurality of the electrodes in the group of electrodes. In some cases, at least one of the clusters may include a single electrode of electrodes 116 of group 402, while one or more other clusters each include a plurality of electrodes 116 of group 402. In particular, one of the clusters produced by the clustering algorithm could have a single electrode. In further examples, generation of clusters with single electrodes could be excluded from the impedance-based allocation process, i.e., prohibited, such that all clusters have multiple electrodes and no clusters have only a single electrode. For example, the clustering algorithm could be configured to exclude generation of clusters with single electrodes for larger sets of electrodes, e.g., more than 8 electrodes, and permit generation of clusters with single electrodes for smaller sets of electrodes, e.g., 8 or less electrodes.

The method also may comprise delivering, e.g., via switch device 206A or 206B, a first portion of the electrical stimulation from a first electrical stimulation source, e.g., stimulation source 202A, of the IMD 100 via the first cluster of electrodes (808), and delivering, e.g., via switch device 206A or 206B, a second portion of the electrical stimulation from a second electrical stimulation source, e.g., stimulation source 202B, of the IMD via the second cluster of electrodes (810). If there are more than two clusters, more than two stimulation sources may deliver respective portions of the electrical stimulation to the respective clusters of electrodes. The portions may have current or voltage amplitudes that are selected to sum to a total desired current or voltage amplitude to be delivered by electrodes 116 in group 402.

Hence, as shown in FIG. 12, the method may comprise delivering a first portion of the electrical stimulation from a first electrical stimulation source 202A of IMD 100A, 100B via a first cluster 404 of one or more electrodes 116, in the group 402 of electrodes, selected based on impedance values of the one or more electrodes in the first cluster, and delivering a second portion of the electrical stimulation from a second electrical stimulation source 202B of the IMD via a second cluster 406 of one or more electrodes, in the group of electrodes, selected based on impedance values of the one or more electrodes in the second cluster.

A method, as shown in FIG. 12, may be performed by IMD 100A, 100B or by a combination of IMD 100A, 100B and external programming device 104. In particular, various aspects of the method may be performed by processor 210 of IMD 100A, 100B or by a combination of processor 210 of the IMD and processor 302 of external programmer 104. As one example, one or more of group 402, first cluster 404 and second cluster 406 (and other clusters as applicable) could be selected with processor 210 of IMD 100A, 100B, processor 302 of external programmer 104, or processors of both the IMD and the external programming device. Hence, one of more of group 402, first cluster 404, second cluster 404, amplitude of the electrical stimulation, and amplitudes of the first and second portions of the stimulation, may be selected with one or more processors of one or both of IMD 100 or external programming device 104 in communication with the IMD.

As an example, with reference to FIG. 12, processor 210 may select the group (802), select the first and second clusters (804, 806), and control switch devices 206A, 206B and stimulation sources 202A, 202B to deliver the first and second portions of the electrical stimulation via the first and second clusters, respectively (808, 810). As another example, processor 302 may select the group (802), and processor 210 may select the first and second clusters (804, 806) and control switch devices 206A, 206B and stimulation sources 202A, 202B to deliver the first and second portions of the electrical stimulation via the first and second clusters, respectively (808, 810). In this case, processor 302 may transmit the group selection to IMD 100, and may also transmit a desired total stimulation amplitude for the group.

As another example, processor 302 may select the group (802) and select the first and second clusters (804, 806), and processor 210 may control switch devices 206A, 206B and stimulation sources 202A, 202B to deliver the first and second portions of the electrical stimulation via the first and second clusters, respectively (808, 810). In this case, processor 210 may transmit measured impedance information to programmer 104 for use in a clustering process performed by processor 302, and processor 302 may transmit the group and cluster selections, or at least the cluster selections, to IMD 100A, 100B. Processor 302 may transmit the desired total amplitude for the group to IMD 100A, 100B, in which case processor 210 may use the total amplitude and the numbers of electrodes in the clusters to determine the amplitudes of the first and second portions of the stimulation to be delivered via the first and second clusters. Alternatively, processor 302 may determine and transmit the amplitudes for the first and second portions of the stimulation to IMD 100A, 100B for use by processor 210. Again, although two clusters are described for purposes of illustration, there may be more than two clusters.

FIG. 12 represents an example of a method and operation of a device or system for impedance-based allocation of stimulation amplitude in accordance with this disclosure. In various examples, a method, device or system as described in this disclosure, e.g., as illustrated in FIG. 12, may be combined with other features or operations. For example, in an example (1), a method, device or system for delivering electrical stimulation to a patient via a plurality of implantable electrodes of an implantable medical device (IMD) delivers a first portion of the electrical stimulation from a first electrical stimulation source of the IMD via a first cluster of one or more electrodes selected based on impedance values of the one or more electrodes in the first cluster, the first cluster of one or more electrodes being in a group of the plurality of implantable electrodes selected for delivery of the electrical stimulation and comprising less than all of the electrodes in the group, and delivers a second portion of the electrical stimulation from a second electrical stimulation source of the IMD via a second cluster of one or more electrodes selected based on impedance values of the one or more electrodes in the second cluster, the second cluster of one or more electrodes being in the group of the plurality of implantable electrodes selected for delivery of the electrical stimulation, being different than the first cluster of one or more electrodes and comprising less than all of the electrodes in the group.

In an example (2), the method, device or system of example (1) may select the group of the plurality of implantable electrodes of the IMD for delivery of the electrical stimulation to the patient, select the first cluster of one or more of the electrodes in the group of the plurality of implantable electrodes based on the impedance values of the one or more electrodes in the first cluster, and select the second cluster of one or more of the electrodes in the group of the plurality of implantable electrodes based on the impedance values of the one or more electrodes in the second cluster.

In an example (3), the method, device or system of either of example (1) or (2) selects the group, the first cluster and the second cluster with one or more processors of at least one of the IMD or an external programmer in communication with the IMD.

In an example (4), the method, device or system of any of examples (1)-(3) measures the impedance values of the electrodes, transmits information representative of the measured impedance values of the electrodes from the IMD to the external programmer, and selects the group, the first cluster, the second cluster, an amplitude of the first portion of the electrical stimulation, and an amplitude of the second portion of the electrical stimulation based on information received from the external programmer.

In an example (5), the method, device or system of any of examples (1)-(4) selects the first and second clusters based on k-means clustering of the electrodes in the group of the plurality of implantable electrodes.

In an example (6), the method, device or system of any of examples (1)-(5) selects amplitudes of the first and second portions of the electrical stimulation such that an average per-electrode amplitude of the electrical stimulation delivered to the one or more electrodes in the first cluster is substantially the same as an average per-electrode amplitude of the electrical stimulation delivered to the one or more electrodes in the second cluster.

In an example (7), in the method, device or system of any of examples (1)-(6), a number of the electrodes in the first cluster is different than a number of the electrodes in the second cluster, and the amplitude of the first portion of the electrical stimulation is different than the amplitude of the second portion of the electrical stimulation.

In an example (8), in the method, device or system of any of examples (1)-(7), selecting the first cluster of one or more electrodes based on impedance values of the electrodes in the first cluster comprises selecting the first cluster of one or more electrodes based on output current values determined for each of the one or more electrodes in the first cluster as a function of the impedance values of the respective one or more electrodes in the first cluster, and selecting the second cluster of one or more electrodes based on impedance values of the electrodes in the second cluster comprises selecting the second cluster of the one or more electrodes based on output current values determined for each of the one or more electrodes in the second cluster as a function of the impedance values of the respective one or more electrodes in the second cluster.

In an example (9), in the method, device or system of any of examples (1)-(8), an amplitude of the first portion of the electrical stimulation and an amplitude of the second portion of the electrical stimulation sum to an amplitude of the electrical stimulation to be delivered via the group of the plurality of implantable electrodes.

In an example (10), in the method, device or system of any of examples (1)-(9), the first cluster comprises a first plurality of the electrodes in the group of the plurality of implantable electrodes and the second cluster comprises a second plurality of the electrodes in the group of the plurality of implantable electrodes.

In an example (11), in the method, device or system of any of examples (1)-(9), one of the first cluster or second cluster comprises a single electrode of the group of the plurality of implantable electrodes.

In an example (12), in the method, device or system of any of examples (1)-(11), the plurality of implantable electrodes are coupled to an implantable pulse generator of the IMD via one or more implantable leads.

In an example (13), in the method, device or system of any of examples (1)-(12), the group of the plurality of implantable electrodes comprises less than all of the plurality of implantable electrodes of the IMD.

In an example (14), in the method, device or system of any of examples (1)-(13), a sum of a number of the electrodes of the first cluster of one or more electrodes and a number of the electrodes of the second cluster of one or more electrodes is equal to a number of the electrodes in the group of the plurality of implantable electrodes.

In an example (15), in the method, device or system of any of examples (1)-(14), the electrodes in the first cluster have a mean impedance value that is less than a mean impedance value of the electrodes in the second cluster.

In an example (16), the method, device or system of any of examples (1)-(15) delivers the first and second portions of the electrical stimulation substantially simultaneously.

In an example (17), the method, device or system of any of examples (1)-(16) measures the impedance values of the electrodes.

In an example (18), the method, device or system of any of examples (1)-(17) controls one or more switch devices to couple each of the electrodes of the first cluster of one or more electrodes to the first electrical stimulation source to deliver the first portion of the electrical stimulation from the first electrical stimulation source via the first cluster of one or more electrodes, and couple each of the electrodes of the second cluster of one or more electrodes to the second electrical stimulation source to deliver the second portion of the electrical stimulation from the second electrical stimulation source via the second cluster of one or more electrodes.

In an example (19), in the method, device or system of any of examples (1)-(18), the electrodes of the plurality of implantable electrodes comprise implantable electrodes coupled to an implantable pulse generator via one or more implantable leads, and each of the impedance values of the electrodes is an impedance value measured between the respective electrode and a reference electrode of the implantable pulse generator.

A non-transitory computer-readable medium, in accordance with this disclosure, may store instructions that, when executed, cause one or more processors, such as processor 210 and/or 302, to perform, or cause IMD 100 or programmer 104, or another device to perform, operations of the methods described in this disclosure, such as the operations of the methods of any of examples (1) through (19) above, alone or in combination. The computer-readable medium may reside, for example, in IMD 100, programmer 104, or in another device, and may be fixed or removable.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units or components may be implemented together or separately as discrete but interoperable logic devices. Depiction of different features as units or components is intended to highlight different functional aspects and does not necessarily imply that such units or components must be realized by separate hardware or software components. Rather, functionality associated with one or more units or components may be performed by separate hardware or software components, or integrated within common or separate hardware or software components.

The techniques described in this disclosure may also be embodied or encoded in a computer-readable medium, such as a non-transitory computer-readable storage medium, containing or storing instructions. Instructions embedded or encoded in a computer-readable storage medium may cause one or more programmable processors to perform any of the methods of this disclosure, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method for delivering electrical stimulation to a patient via a plurality of implantable electrodes of an implantable medical device (IMD), the method comprising:
    delivering a first portion of the electrical stimulation generated from a first electrical stimulation source of the IMD via a first cluster of one or more electrodes selected based on impedance values of the one or more electrodes in the first cluster, the first cluster of one or more electrodes being in a group of the plurality of implantable electrodes selected for delivery of the electrical stimulation and comprising less than all of the electrodes in the group; and delivering a second portion of the electrical stimulation generated from a second electrical stimulation source of the IMD via a second cluster of one or more electrodes selected based on impedance values of the one or more electrodes in the second cluster, the second cluster of one or more electrodes being in the group of the plurality of implantable electrodes selected for delivery of the electrical stimulation, being different than the first cluster of one or more electrodes and comprising less than all of the electrodes in the group.

2. The method of claim 1, further comprising:
selecting the group of the plurality of implantable electrodes of the IMD for delivery of the electrical stimulation to the patient;
selecting the first cluster of one or more of the electrodes in the group of the plurality of implantable electrodes based on the impedance values of the one or more electrodes in the first cluster; and
selecting the second cluster of one or more of the electrodes in the group of the plurality of implantable electrodes based on the impedance values of the one or more electrodes in the second cluster.

3. The method of claim 2, further comprising selecting the group, the first cluster and the second cluster with one or more processors of at least one of the IMD or an external programmer in communication with the IMD.

4. The method of claim 3, further comprising measuring the impedance values of the electrodes, transmitting information representative of the measured impedance values of the electrodes from the IMD to the external programmer, and selecting the group, the first cluster, the second cluster, an amplitude of the first portion of the electrical stimulation, and an amplitude of the second portion of the electrical stimulation based on information received from the external programmer.

5. The method of claim 2, wherein selecting the first and second clusters comprises selecting the first and second clusters based on k-means clustering of the electrodes in the group of the plurality of implantable electrodes.

6. The method of claim 2, further comprising selecting amplitudes of the first and second portions of the electrical stimulation such that an average per-electrode amplitude of the electrical stimulation delivered to the one or more electrodes in the first cluster is substantially the same as an average per-electrode amplitude of the electrical stimulation delivered to the one or more electrodes in the second cluster.

7. The method of claim 6, wherein a number of the electrodes in the first cluster is different than a number of the electrodes in the second cluster, and wherein the amplitude of the first portion of the electrical stimulation is different than the amplitude of the second portion of the electrical stimulation.

8. The method of claim 2, wherein:
selecting the first cluster of one or more electrodes based on impedance values of the electrodes in the first cluster comprises selecting the first cluster of one or more electrodes based on output current values determined for each of the one or more electrodes in the first cluster as a function of the impedance values of the respective one or more electrodes in the first cluster; and
selecting the second cluster of one or more electrodes based on impedance values of the electrodes in the second cluster comprises selecting the second cluster of the one or more electrodes based on output current values determined for each of the one or more electrodes in the second cluster as a function of the impedance values of the respective one or more electrodes in the second cluster.

9. The method of claim 1, wherein an amplitude of the first portion of the electrical stimulation and an amplitude of the second portion of the electrical stimulation sum to an amplitude of the electrical stimulation to be delivered via the group of the plurality of implantable electrodes.

10. The method of claim 1, wherein the first cluster comprises a first plurality of the electrodes in the group of the plurality of implantable electrodes and the second cluster comprises a second plurality of the electrodes in the group of the plurality of implantable electrodes.

11. The method of claim 1, wherein one of the first cluster or second cluster comprises a single electrode of the group of the plurality of implantable electrodes.

12. The method of claim 1, wherein the plurality of implantable electrodes are coupled to an implantable pulse generator of the IMD via one or more implantable leads.

13. The method of claim 1, wherein the group of the plurality of implantable electrodes comprises less than all of the plurality of implantable electrodes of the IMD.

14. The method of claim 1, wherein a sum of a number of the electrodes of the first cluster of one or more electrodes and a number of the electrodes of the second cluster of one or more electrodes is equal to a number of the electrodes in the group of the plurality of implantable electrodes.

15. The method of claim 1, wherein the electrodes in the first cluster have a mean impedance value that is less than a mean impedance value of the electrodes in the second cluster.

16. The method of claim 1, further comprising delivering the first and second portions of the electrical stimulation substantially simultaneously.

17. The method of claim 1, further comprising measuring the impedance values of the electrodes.

18. The method of claim 1, further comprising controlling one or more switch devices to couple each of the electrodes of the first cluster of one or more electrodes to the first electrical stimulation source to deliver the first portion of the electrical stimulation from the first electrical stimulation source via the first cluster of one or more electrodes, and couple each of the electrodes of the second cluster of one or more electrodes to the second electrical stimulation source to deliver the second portion of the electrical stimulation from the second electrical stimulation source via the second cluster of one or more electrodes.

19. The method of claim 1, wherein the electrodes of the plurality of implantable electrodes comprise implantable electrodes coupled to an implantable pulse generator via one or more implantable leads, and wherein each of the impedance values of the electrodes is an impedance value measured between the respective electrode and a reference electrode of the implantable pulse generator.

20. An implantable medical device (IMD) for delivering electrical stimulation to a patient, the IMD comprising:
a plurality of implantable electrodes;
a first electrical stimulation source configured to generate a first portion of the electrical stimulation;
a second electrical stimulation source configured to generate a second portion of the electrical stimulation; and
one or more processors configured to:
control the first electrical stimulation source to deliver the first portion of the electrical stimulation via a first cluster of one or more electrodes selected based on impedance values of the one or more electrodes in the first cluster, the first cluster of one or more electrodes being in a group of the plurality of implantable electrodes selected for delivery of the electrical stimulation and comprising less than all of the electrodes in the group; and control the second electrical stimulation source to deliver the second portion of the electrical stimulation via a second cluster of one or more electrodes selected based on impedance values of the one or more electrodes in the second cluster, the second cluster of one or more electrodes being in the group of the plurality of implantable electrodes selected for delivery of the electrical stimulation, being different than the first cluster of one or more electrodes and comprising less than all of the electrodes in the group.

21. The IMD of claim 20, wherein the one or more processors are configured to:

select the group of the plurality of implantable electrodes of the IMD for delivery of the electrical stimulation to the patient;

select the first cluster of one or more of the electrodes in the group of the plurality of implantable electrodes based on the impedance values of the one or more electrodes in the first cluster; and select the second cluster of one or more of the electrodes in the group of the plurality of implantable electrodes based on the impedance values of the one or more electrodes in the second cluster.

22. The IMD of claim 21, further comprising a sensing circuit configured to measure the impedance values of the electrodes and a telemetry interface, wherein the one or more processors are configured to control the telemetry interface to transmit information representative of the measured impedance values of the electrodes from the IMD to an external programmer, and select the group, the first cluster, the second cluster, an amplitude of the first portion of the electrical stimulation, and an amplitude of the second portion of the electrical stimulation based on information received from the external programmer via the telemetry interface.

23. The IMD of claim 21, wherein the one or more processors are configured to select the first and second clusters based on k-means clustering of the electrodes in the group of the plurality of implantable electrodes.

24. The IMD of claim 21, wherein the one or more processors are configured to select amplitudes of the first and second portions of the electrical stimulation such that an average per-electrode amplitude of the electrical stimulation delivered to the one or more electrodes in the first cluster is substantially the same as an average per-electrode amplitude of the electrical stimulation delivered to the one or more electrodes in the second cluster.

25. The IMD of claim 24, wherein a number of the electrodes in the first cluster is different than a number of the electrodes in the second cluster, and wherein the amplitude of the first portion of the electrical stimulation is different than the amplitude of the second portion of the electrical stimulation.

26. The IMD of claim 21, wherein the one or more processors are configured to:

select the first cluster of one or more electrodes based on output current values determined for each of the one or more electrodes in the first cluster as a function of the impedance values of the respective one or more electrodes in the first cluster; and select the second cluster of the one or more electrodes based on output current values determined for each of the one or more electrodes in the second cluster as a function of the impedance values of the respective one or more electrodes in the second cluster.

27. The IMD of claim 20, wherein an amplitude of the first portion of the electrical stimulation and an amplitude of the second portion of the electrical stimulation sum to an amplitude of the electrical stimulation to be delivered via the group of the plurality of implantable electrodes.

28. The IMD of claim 20, wherein the first cluster comprises a first plurality of the electrodes in the group of the plurality of implantable electrodes and the second cluster comprises a second plurality of the electrodes in the group of the plurality of implantable electrodes.

29. The IMD of claim 20, wherein one of the first cluster or second cluster comprises a single electrode of the group of the plurality of implantable electrodes.

30. The IMD of claim 20, further comprising:

an implantable pulse generator comprising the first and second stimulation sources; and one or more implantable leads coupled to the implantable pulse generator, wherein the electrodes comprise implantable electrodes coupled to the implantable pulse generator via the one or more implantable leads.

31. The IMD of claim 20, wherein the group of the plurality of implantable electrodes comprises less than all of the plurality of implantable electrodes of the IMD.

32. The IMD of claim 20, wherein a sum of a number of the electrodes of the first cluster and a number of the electrodes of the second cluster is equal to a number of the electrodes in the group of the plurality of implantable electrodes.

33. The IMD of claim 20, wherein the electrodes in the first cluster have a mean impedance value that is less than a mean impedance value of the electrodes in the second cluster.

34. The IMD of claim 20, wherein the one or more processors are configured to control the first and second electrical stimulation sources to deliver the first and second portions of the electrical stimulation substantially simultaneously.

35. The IMD of claim 20, further comprising a sensing circuit configured to measure the impedance values of the electrodes.

36. The IMD of claim 20, further comprising one or more switch devices, wherein the one or more processors are configured to control the one or more switch devices to couple each of the electrodes of the first cluster of one or more electrodes to the first electrical stimulation source to deliver the first portion of the electrical stimulation from the first electrical stimulation source via the first cluster of one or more electrodes, and couple each of the electrodes of the second cluster of one or more electrodes to the second electrical stimulation source to deliver the second portion of the electrical stimulation from the second electrical stimulation source via the second cluster of one or more electrodes.

37. The IMD of claim 20, further comprising:

an implantable pulse generator comprising the first and second stimulation sources; and one or more implantable leads coupled to the implantable pulse generator, wherein the plurality of implantable electrodes comprise implantable electrodes coupled to the implantable electrical stimulation generator via the implantable lead, and wherein each of the impedance values of the electrodes is an impedance value measured between the respective electrode and a reference electrode of the implantable pulse generator.

38. A system for delivering electrical stimulation to a patient, the system comprising:
an implantable medical device (IMD) comprising:
a plurality of implantable electrodes,
a first electrical stimulation source configured to generate a first portion of the electrical stimulation,
a second electrical stimulation source configured to generate a second portion of the electrical stimulation, and
one or more processors configured to:
control the first electrical stimulation source to deliver the first portion of the electrical stimulation via a first cluster of one or more electrodes selected based on impedance values of the one or more electrodes in the first cluster, the first cluster of one or more electrodes being in a group of the plurality of implantable electrodes selected for delivery of the electrical stimulation and comprising less than all of the electrodes in the group, and
control the second electrical stimulation source to deliver the second portion of the electrical stimulation via a second cluster of one or more electrodes selected based on impedance values of the one or more electrodes in the second cluster, the second cluster of one or more electrodes being in the group of the plurality of implantable electrodes selected for delivery of the electrical stimulation, being different than the first cluster of one or more electrodes and comprising less than all of the electrodes in the group; and
an external programmer comprising one or more processors configured to program one or more parameters of the electrical stimulation delivered by the IMD,
wherein one or more processors of at least one of the IMD or the external programmer are configured to:
select the group of the plurality of implantable electrodes of the IMD for delivery of the electrical stimulation to the patient,
select the first cluster of one or more of the electrodes in the group of the plurality of implantable electrodes based on the impedance values of the one or more electrodes in the first cluster, and
select the second cluster of one or more of the electrodes in the group of the plurality of implantable electrodes based on the impedance values of the one or more electrodes in the second cluster.

39. The system of claim 38, wherein the IMD further comprises a sensing circuit configured to measure the impedance values of the electrodes and a telemetry interface, wherein the one or more processors of the IMD are configured to control the telemetry interface to transmit information representative of the measured impedance values of the electrodes from the IMD to the external programmer, and select the group, the first cluster, the second cluster, an amplitude of the first portion of the electrical stimulation, and an amplitude of the second portion of the electrical stimulation based on information received from the external programmer via the telemetry interface.

40. A system for delivering electrical stimulation to a patient via a plurality of implantable electrodes of an implantable medical device (IMD), the system comprising:
means for selecting a group of the plurality of implantable electrodes of the IMD for delivery of the electrical stimulation to the patient;
means for selecting a first cluster of one or more of the electrodes in the group of the plurality of implantable electrodes based on impedance values of the electrodes in the first cluster, the first cluster of electrodes comprising less than all of the electrodes in the group of the plurality of implantable electrodes;
means for selecting a second cluster of one or more of the electrodes in the group of the plurality of implantable electrodes based on impedance values of the electrodes in the second cluster, the second cluster of electrodes being different than the first cluster of electrodes and comprising less than all of the electrodes in the group of the plurality of implantable electrodes;
means for delivering a first portion of the electrical stimulation from a first electrical stimulation source of the IMD via the first cluster of electrodes; and
means for delivering a second portion of the electrical stimulation from a second electrical stimulation source of the IMD via the second cluster of electrodes.

41. The system of claim 40, further comprising means for programming one or more parameters of the electrical stimulation delivered by the first and second electrical stimulation sources of the IMD.

* * * * *